United States Patent
Huynh

(10) Patent No.: US 11,187,651 B2
(45) Date of Patent: Nov. 30, 2021

(54) METHODS AND DEVICES FOR IMPROVED SIGNAL DETECTION FROM BIOLOGICAL SAMPLES

(71) Applicant: Theranos IP Company, LLC, Healdsburg, CA (US)

(72) Inventor: Toan Huynh, Mountain View, CA (US)

(73) Assignee: Labrador Diagnostics LLC, Wilmington, DE (US)

( * ) Notice: Subject to any disclaimer, the term of this patent is extended or adjusted under 35 U.S.C. 154(b) by 0 days.

(21) Appl. No.: 16/527,473

(22) Filed: Jul. 31, 2019

(65) Prior Publication Data

US 2020/0049622 A1 Feb. 13, 2020

Related U.S. Application Data

(63) Continuation of application No. PCT/US2018/016292, filed on Jan. 31, 2018.
(Continued)

(51) Int. Cl.
*G01N 21/33* (2006.01)
*G01N 33/49* (2006.01)

(52) U.S. Cl.
CPC .............. *G01N 21/33* (2013.01); *G01N 33/49* (2013.01)

(58) Field of Classification Search
CPC .............. G01N 35/00732; G01N 21/31; G01N 35/00603; G01N 2035/00752; G01N 35/04; G01N 2035/0406; G01N 2035/0493; G01N 21/59; G01N 2201/062; G01N 33/49; G01N 35/0099; G01N 35/025; G01N 21/255; G01N 30/02; G01N 35/00594; G01N 35/02; G01N 2035/1018; G01N 2035/1025; G01N 21/0332; G01N 21/25; G01N 21/253; G01N 21/27; G01N 2201/12; G01N 2560/00; G01N 33/6848; G01N 33/86; G01N 35/1016; G01N 15/042; G01N 15/05;
(Continued)

(56) References Cited

U.S. PATENT DOCUMENTS 6,340,744 B1 * 1/2002 Leif ................. C07D 471/18
424/9.6
6,556,853 B1 * 4/2003 Cabib ................. A61B 5/14555
351/221
(Continued)

OTHER PUBLICATIONS

"Optical Non-Invasive Estimation and Mapping of Skin Bilirubin, Hemoglobin and Water"; University of Latvia Institute of Atomic Physics and Spectroscopy; Inga Saknite (2015).*
(Continued)

*Primary Examiner* — Michael P Stafira

(57) ABSTRACT

Methods and devices are provided to provide clean signals even in the presence of spectral interference. At least some of these methods can be applied for cases when interfering signals are to be accounted for. These cases include, but are not limited to, hemolysis detection, icterus detection, and assays. They can be implemented in with data collected with spectrophotometers, instruments that can collect absorbance values at the few wavelengths of interest, and, in the case of the method based on background subtraction, simple imaging setups with only two filters (such as but not limited to narrow-band and wide-band) per absorption peak of interest.

3 Claims, 17 Drawing Sheets

Related U.S. Application Data

(60) Provisional application No. 62/519,018, filed on Jun. 13, 2017, provisional application No. 62/452,949, filed on Jan. 31, 2017.

(58) Field of Classification Search
CPC ......... G01N 2035/00465; G01N 21/03; G01N 21/17; G01N 21/51; G01N 21/90; G01N 2201/0231; G01N 2201/0627; G01N 2333/47; G01N 30/72; G01N 33/5302; G01N 35/026; G01N 35/1011; G01N 2015/055; G01N 2035/0467; G01N 2035/0491; G01N 2035/0494; G01N 2035/1062; G01N 21/00; G01N 21/251; G01N 21/314; G01N 21/82; G01N 21/9036; G01N 2201/10; G01N 33/483; G01N 33/491; G01N 33/492; G01N 33/721; G01N 35/00; G01N 35/00613; G01N 35/00663; G01N 35/00871; G01N 2015/045; G01N 2015/047; G01N 2021/0346; G01N 2021/3148; G01N 2021/825; G01N 2021/845; G01N 2021/8861; G01N 2021/8887; G01N 2030/8813; G01N 2030/8822; G01N 2030/8831; G01N 2035/00326; G01N 2035/00801; G01N 2035/0401; G01N 2035/0403; G01N 2035/0455; G01N 2035/0465; G01N 2035/047; G01N 2035/1039; G01N 21/01; G01N 21/274; G01N 21/55; G01N 21/63; G01N 21/73; G01N 21/9027; G01N 2201/02; G01N 2201/064; G01N 2201/1293; G01N 2333/575; G01N 2333/62; G01N 2333/635; G01N 2800/042; G01N 30/88; G01N 33/5306; G01N 33/538; G01N 33/539; G01N 33/541; G01N 33/564; G01N 33/728; G01N 33/74; G01N 33/78; G01N 33/82; G01N 33/84; G01N 33/92; G01N 35/00584; G01N 35/00693; G01N 35/0092; G01N 35/10; G01N 1/34; G01N 2015/0065; G01N 2021/1772; G01N 2021/1776; G01N 2021/3129; G01N 2021/3137; G01N 2021/3155; G01N 2021/3174; G01N 2021/5923; G01N 2021/5957; G01N 2021/5969; G01N 2021/6482; G01N 2021/8514; G01N 2021/8521; G01N 2021/8528; G01N 2021/8535; G01N 2021/8845; G01N 2030/027; G01N 2030/045; G01N 2035/00356; G01N 2035/00495; G01N 2035/00633; G01N 2035/00702; G01N 2035/00772; G01N 2035/00821; G01N 2035/00881; G01N 2035/0439; G01N 2035/0441; G01N 2035/103; G01N 21/13; G01N 21/15; G01N 21/272; G01N 21/278; G01N 21/33; G01N 21/359; G01N 21/41; G01N 21/474; G01N 21/78; G01N 21/84; G01N 21/8507; G01N 21/88; G01N 21/909; G01N 21/94; G01N 2201/0618; G01N 2201/0634; G01N 2201/0635; G01N 2201/0806; G01N 2201/0826; G01N 2201/101; G01N 2201/1296; G01N 2333/4703; G01N 2405/02; G01N 2800/04; G01N 2800/347; G01N 2800/52; G01N 30/04; G01N 30/7233; G01N 33/487; G01N 33/48707; G01N 33/4905; G01N 33/52; G01N 33/54313; G01N 33/54346; G01N 33/54393; G01N 33/573; G01N 33/6827; G01N 33/6842; G01N 33/743; G01N 11/00; G01N 11/245; G01N 11/06; G01N 3/2823; G01N 2003/104; G01N 2003/106; G01N 2003/123; G01N 2003/2826; G01N 3/0208; G01N 3/10; G01N 3/108; G01N 3/462; G01N 3/50; G01B 11/00; G01B 11/245; G01B 11/06; G01J 3/2823; G01J 2003/104; G01J 2003/106; G01J 2003/123; G01J 2003/2826; G01J 3/0208; G01J 3/10; G01J 3/108; G01J 3/462; G01J 3/50; G01N 21/6428; G01N 21/6458; G01N 2021/6439; G01N 33/6896; G01N 33/582; G01N 1/40; G01N 2333/4709; G01N 27/44791; G01N 33/56911; G01N 2015/1006; G01N 2800/28; G01N 2800/2821; G01N 33/5308; G01N 33/533; G01N 1/30; G01N 21/658; G01N 2800/387; G01N 33/4833; G01N 33/5058; G01N 33/532; G01N 33/543; G01N 33/54386; G01N 33/58; G01N 33/68; G01N 15/1434; G01N 15/1456; G01N 15/1459; G01N 15/147; G01N 15/1475; G01N 1/38; G01N 2001/028; G01N 2015/0084; G01N 2015/1445; G01N 2015/1486; G01N 2015/149; G01N 2021/6463; G01N 21/6445; G01N 21/6456; G01N 21/76; G01N 2201/126; G01N 2333/4716; G01N 2333/55; G01N 2333/57; G01N 2333/70532; G01N 2333/70578; G01N 2333/72; G01N 2333/96425; G01N 2405/10; G01N 2440/14; G01N 2458/00; G01N 2458/10; G01N 2458/30; G01N 2500/00; G01N 27/30; G01N 27/4145; G01N 27/4148; G01N 2800/26; G01N 2800/2835; G01N 2800/368; G01N 2800/50; G01N 2800/7028; G01N 33/48; G01N 33/5005; G01N 33/5008; G01N 33/5014; G01N 33/5023; G01N 33/5047; G01N 33/5076; G01N 33/5088; G01N 33/5091; G01N 33/53; G01N 33/531; G01N 33/534; G01N 33/535; G01N 33/542; G01N 33/54326; G01N 33/54333; G01N 33/5438; G01N 33/552; G01N 33/553; G01N 33/558; G01N 33/563; G01N 33/56972; G01N 33/56983; G01N 33/57407; G01N 33/57423; G01N 33/5743; G01N 33/57492; G01N 33/57496; G01N 33/581; G01N 33/587; G01N 33/6845; G01N 33/6851; G01N 33/6854; G01N 33/6872; G01N 33/6875; G01N 33/689

See application file for complete search history.

(56) References Cited

U.S. PATENT DOCUMENTS 6,690,817 B1 * 2/2004 Cabib ................ G01B 11/0675
382/134
2015/0044780 A1 * 2/2015 Kurz ................ G01N 33/54393
436/501

(56) References Cited

U.S. PATENT DOCUMENTS

2015/0132789 A1* 5/2015 Bornheimer ....... G01N 21/6428
                                                    435/29
2015/0168371 A1* 6/2015 Babson .................. G01N 33/49
                                                    356/40
2018/0059006 A1* 3/2018 Fritchie ................ G01N 21/255

OTHER PUBLICATIONS

Blakney et al. A spectrophotometric scanning technique for the rapid determination of plasma hemoglobin, 1975, Clin. Bioehem., vol. 8, pp. 96-102.

Enejder et al. Blood analysis by Raman spectroscopy. Optics Letters, 2002, vol. 27, No. 22, pp. 2004-2006.

International Search Report dated Jun. 14, 2018 for PCT/US2018/016292.

Kasagani V. K, Optical Quantification of Hemolysis, Icterus, and Lipemia in Human Serum, a thesis submitted to the faculty of The University of Utah in partial fulfillment of the requirements for the degree of Master of Science, Dec. 2013, pp. 1-68.

Liu, et al. Extraction of Target Fluorescence Signal from In Vivo Background Signal Using Image Subtraction Algorithm. International Journal of Automation and Computing, 2012, vol. 9, No. 3, pp. 232-236.

Wang et al. A method for accurate in vivo micro-Raman spectroscopic measurements under guidance of advanced microscopy imaging, Scientific Reports, 2013, vol. 3, Article No. 1890, pp. 1-6.

* cited by examiner

METHODS AND DEVICES FOR IMPROVED SIGNAL DETECTION FROM BIOLOGICAL SAMPLES

BACKGROUND

Hemolysis, icterus, and lipemia are indicated by different features in the absorption spectra of some detection systems and may interfere with one another in a negative manner. The detection/quantification of each of these interference types alone is straightforward, but is complicated when multiple types of interference are present. For example, hemolysis is caused by the lysis of blood cells before the separation to obtain plasma/serum, and is indicated by the concentration of hemoglobin (Hb) from red blood cells. The Hb concentration can be estimated by the absorbance signals near peaks at 340-440 nm and 540-580 nm. Icterus is the interference caused by the presence of bilirubin, which absorbs light with a peak around 460 nm and does not significantly interfere with hemolysis signals in the 540-580 nm range. Lipemia is the interference by the presence of lipid particles, which scatter light and lead to the apparent absorption across a wide range of the UV-Vis spectrum (400-800+ nm). Due to the close proximity of their peak signal wavelengths, the hemolysis and icterus peaks partially overlap with each other, and the lipemia absorption increase affects the whole spectra. Example commercial systems utilize absorbance values at wavelengths from 340 nm to 800 nm and complicated calibration procedures to account for this issue.

Known techniques have various drawbacks and are overly cumbersome and costly in their implementation.

INCORPORATION BY REFERENCE

All publications, patents, and patent applications mentioned in this specification are herein incorporated by reference to the same extent as if each individual publication, patent, or patent application was specifically and individually indicated to be incorporated by reference.

COPYRIGHT

This document contains material subject to copyright protection. The copyright owner (Applicant herein) has no objection to facsimile reproduction of the patent documents and disclosures, as they appear in the US Patent and Trademark Office patent file or records, but otherwise reserves all copyright rights whatsoever. The following notice shall apply: Copyright 2016-2018 Theranos, Inc.

SUMMARY

The disadvantages associated with the prior art are overcome by embodiments described herein.

In one embodiment herein, it is desirable to detect/quantify hemolysis, icterus, and lipemia (common types of interference) in plasma/serum clinical samples. Some methods utilize absorbance values of the samples at multiple wavelengths to account for the cross signals. They use calibration sample sets that span possible ranges of these interference types and instruments that can measure absorbance values across the whole UV-vis wavelength range.

In one embodiment, new methods are described herein to detect/quantify hemolysis and/or icterus (two out of the three interference types) that are based on absorbance values at narrower wavelength ranges, use fewer samples for calibration, and/or are independent of the nature of the interference.

At least some embodiments of the new methods described here aim to eliminate spectral interfering signals and obtain clean final signals. With a first non-limiting example, the final signal is the curvature at the peak of interest in the absorption spectrum. With a second non-limiting example, the final signal, termed background-subtracted signal, is the difference between the raw (original/major) absorbance and the background absorbance in the vicinity of the peak of interest.

In one embodiment, a method is provided for use with a biological sample, the method comprising using peak curvature to reduce interference in detection of hemolysis in the biological sample. Optionally, the method comprises using peak curvature to reduce interference in quantification of hemolysis in the biological sample.

In another embodiment, a method is provided for use with a biological sample, the method comprising using background subtraction in the detection of hemolysis and icterus in the biological sample. Optionally, the method comprises using background subtraction in the quantification of hemolysis and icterus in the biological sample.

In yet another embodiment, a method is provided for use with a biological sample, the method comprising reducing signal interference through calculation of background-subtracted spectra.

In yet another embodiment, a method is provided for use with a biological sample, the method comprising: acquiring background-subtracted signals using a narrow-band optical filter and a wide-band optical filter; and using background-subtracted signals for quantification of hemolysis and icterus in the biological sample. Optionally, the method comprises placing the narrow-band optical filter and the wide-band optical filter in regions of interest concurrently so that only one exposure is needed to obtain the major signal, the background signal, and the background-subtracted signal.

It should be understood that embodiments in this disclosure may be adapted to have one or more of the features described below. In one nonlimiting example, the sample may be plasma. Optionally, in some embodiments, the sample may be serum. Optionally, in some embodiments, any of the foregoing may be from capillary blood. Optionally, in some embodiments, any of the foregoing may be from venous whole blood. Optionally, in some embodiments, the sample may be capillary blood. Optionally, in some embodiments, the sample may be venous whole blood.

In one embodiment, the methods based on curvature calculation and background subtraction can give clean signals even in the presence of spectral interference. At least some of these methods can be applied for cases when interfering signals are to be accounted for. These cases include, but are not limited to, hemolysis detection, icterus detection, and assays. They can be implemented in with data collected with spectrophotometers, instruments that can collect absorbance values at the few wavelengths of interest, and, in the case of the method based on background subtraction, simple imaging setups with only two filters (such as but not limited to narrow-band and wide-band) per absorption peak of interest.

By way of example and not limitation, the potential applications of the methods described here include, but are not limited to, the following:

Clinical or point-of-care use: hemolysis detection/quantification, icterus detection/quantification, and/or assays;

Research & development experiments: hemolysis detection/quantification, icterus detection/quantification, and/or assays;

At the sample collection sites: hemolysis detection/quantification, icterus detection/quantification in samples collected.

In at least one embodiment, the processed signals correlated well with concentrations of hemoglobin and bilirubin, indicators of hemolysis and icterus, respectively. Through iterations of randomly splitting the samples for calibration and testing, the two new methods performed as well as those used on conventional analyzers. By way of non-limiting example, it was demonstrated that the two of the embodiments of the methods can each lessen the application requirements of 1) prior knowledge of the absorption spectra of individual interferents, 2) calibration over a wide concentration range for each interferent, and 3) the need for full-range spectrophotometers spanning most of the ultraviolet/visible spectrum. We also proposed a hardware setup to detect and quantify hemolysis or icterus with a camera and two optical filters.

It should be understood that traditional methods utilize absorbance values at multiple wavelengths to account for potentially interfering signals from other interferents. They require calibrations that span possible concentration ranges of these interferents and instruments that can measure absorbance values across the ultraviolet/visible wavelength range. This paper describes two new methods to quantify and detect hemolysis and icterus (two of the three interferents) that have fewer requirements in development and implementation.

By way of non-limiting example, at least some embodiments of the method involve calculating either the background-subtracted signals or curvatures from spectral data. The advantages of these new methods are three-fold: 1) the elimination of the need to know beforehand how other interferents affect the detection and quantification of the interferent being investigated, 2) fewer samples required for calibration, and 3) fewer constraints on hardware design (thanks to the narrower ranges of required wavelengths).

In one embodiment, a method for sample processing which may include one or more the techniques as described herein for handling sample that may contain interferents. Optionally, a method is provided comprising at least one technical feature described herein. Optionally, a method is provided comprising at least one technical feature from any of the prior features. Optionally, the method comprises at least any two technical features from any of the prior features. Optionally, a device is provided comprising at least one technical feature from any of the prior features. Optionally, the device comprises at least any two technical features from any of the prior features. Optionally, the system is provided comprising at least one technical feature from any of the prior features. Optionally, the system comprises at least any two technical features from any of the prior features.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

DESCRIPTION OF THE SPECIFIC EMBODIMENTS

Figure 1:
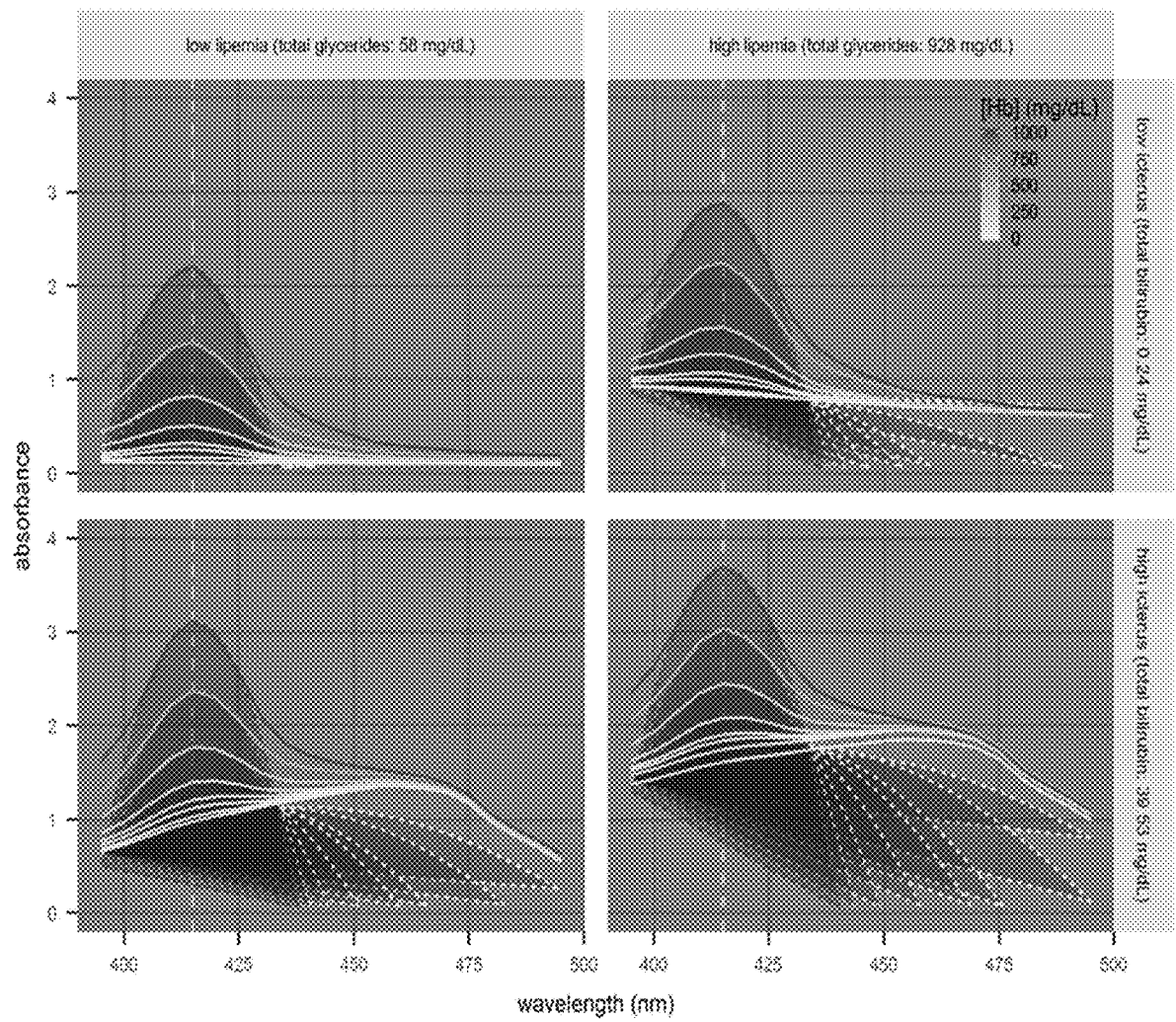
FIG. 1 shows the use of peak curvatures to reduce spectral interference according to at least one embodiment herein.

It is to be understood that both the foregoing general description and the following detailed description are exemplary and explanatory only and are not restrictive of the invention, as claimed. It may be noted that, as used in the specification and the appended claims, the singular forms "a", "an" and "the" include plural referents unless the context clearly dictates otherwise. Thus, for example, reference to "a material" may include mixtures of materials, reference to "a compound" may include multiple compounds, and the like. References cited herein are hereby incorporated by reference in their entirety, except to the extent that they conflict with teachings explicitly set forth in this specification.

In this specification and in the claims which follow, reference will be made to a number of terms which shall be defined to have the following meanings:

"Optional" or "optionally" means that the subsequently described circumstance may or may not occur, so that the description includes instances where the circumstance occurs and instances where it does not. For example, if a device optionally contains a feature for a sample collection unit, this means that the sample collection unit may or may not be present, and, thus, the description includes both structures wherein a device possesses the sample collection unit and structures wherein sample collection unit is not present.

As used herein, the terms "substantial" means more than a minimal or insignificant amount; and "substantially" means more than a minimally or insignificantly. Thus, for example, the phrase "substantially different", as used herein, denotes a sufficiently high degree of difference between two numeric values such that one of skill in the art would consider the difference between the two values to be of statistical significance within the context of the characteristic measured by said values. Thus, the difference between two values that are substantially different from each other is typically greater than about 10%, and may be greater than about 20%, preferably greater than about 30%, preferably greater than about 40%, preferably greater than about 50% as a function of the reference value or comparator value.

As used herein, a "sample" may be but is not limited to a blood sample, or a portion of a blood sample, may be of any suitable size or volume, and is preferably of small size or volume. In some embodiments of the assays and methods disclosed herein, measurements may be made using a small volume blood sample, or no more than a small volume portion of a blood sample, where a small volume comprises no more than about 5 mL; or comprises no more than about 3 mL; or comprises no more than about 2 mL; or comprises no more than about 1 mL; or comprises no more than about 500 µL; or comprises no more than about 250 µL; or comprises no more than about 100 µL; or comprises no more than about 75 µL; or comprises no more than about 50 µL; or comprises no more than about 35 µL; or comprises no more than about 25 µL; or comprises no more than about 20 µL; or comprises no more than about 15 µL; or comprises no more than about 10 µL; or comprises no more than about 8 µL; or comprises no more than about 6 µL; or comprises no more than about 5 µL; or comprises no more than about 4 µL; or comprises no more than about 3 µL; or comprises no more than about 2 µL; or comprises no more than about 1 µL; or comprises no more than about 0.8 µL; or comprises no more than about 0.5 µL; or comprises no more than about 0.3 µL; or comprises no more than about 0.2 µL; or comprises no more than about 0.1 µL; or comprises no more than about 0.05 µL; or comprises no more than about 0.01 µL.

As used herein, the term "point of service location" may include locations where a subject may receive a service (e.g. testing, monitoring, treatment, diagnosis, guidance, sample collection, ID verification, medical services, non-medical services, etc.), and may include, without limitation, a subject's home, a subject's business, the location of a healthcare provider (e.g., doctor), hospitals, emergency rooms, operating rooms, clinics, health care professionals' offices, laboratories, retailers [e.g. pharmacies (e.g., retail pharmacy, clinical pharmacy, hospital pharmacy), drugstores, supermarkets, grocers, etc.], transportation vehicles (e.g. car, boat, truck, bus, airplane, motorcycle, ambulance, mobile unit, fire engine/truck, emergency vehicle, law enforcement vehicle, police car, or other vehicle configured to transport a subject from one point to another, etc.), traveling medical care units, mobile units, schools, day-care centers, security screening locations, combat locations, health assisted living residences, government offices, office buildings, tents, bodily fluid sample acquisition sites (e.g. blood collection centers), sites at or near an entrance to a location that a subject may wish to access, sites on or near a device that a subject may wish to access (e.g., the location of a computer if the subject wishes to access the computer), a location where a sample processing device receives a sample, or any other point of service location described elsewhere herein.

Using Peak Curvature to Avoid Interference in the Detection/Quantification of Hemolysis For at least one non-limiting example, it should be understood that the shape of a specific absorption peak (e.g. the 415-nm hemoglobin peak) does not change if there is interference by a nearby peak (e.g. the 460-nm bilirubin peak) or by an increase in absorption across a wide range of wavelengths (e.g. in the case of lipemia). To demonstrate this, spectra of multiple samples at different levels hemolysis, icterus, and lipemia were acquired. With each spectrum, at the 415-nm peak, the circle center $\vec{M}$ and the corresponding radius of curvature R were determined by fitting to 5 data points at 405, 410, 415, 420, and 425 nm ($\vec{X}_i$) using the cost function specified in Equation 1. Other numbers of points ($\geq 3$) can be used for the fitting; and if only 3 data points (e.g. those at 410, 415, and 240 nm) are used, the center $\vec{M}$ and the radius R can be calculated exactly. The curvature of the hemolysis peak at 415 nm, K, is the inverse of the radius of the curvature, and is insensitive to icterus and lipemia. Therefore, the curvature K is a quantity that can be independently and reliably used for the detection/quantification of hemolysis in the presence of icterus/lipemia. Other methods of calculating the curvatures can also be used.

$$\text{Cost} = \Sigma_{i=1}^{i=5} (\|\vec{M} - \vec{X}_i\| - R)^2 \qquad \text{Equation 1}$$

Referring now to FIG. 1, peak curvatures are used to reduce spectral interference from icterus and lipemia in hemolysis detection/quantification. The plots show absorption spectra near the major hemoglobin peak (415 nm, dashed-line) of samples at different hemolysis levels ([Hb] of 0-1000 mg/dL) at combinations of low and high icterus and lipemia (total bilirubin=0.24 or 39.53 mg/dL; total glycerides=58 or 928 mg/dL). The blue shaded areas indicate circles fitted to the sets of 5 points centered at the 415-nm peak using Equation 1 (see above). The circles appear to be ellipses because of the different in scales of the absorbance and the wavelength. Each curvature value is the inverse of the corresponding radius.

Figure 1A:
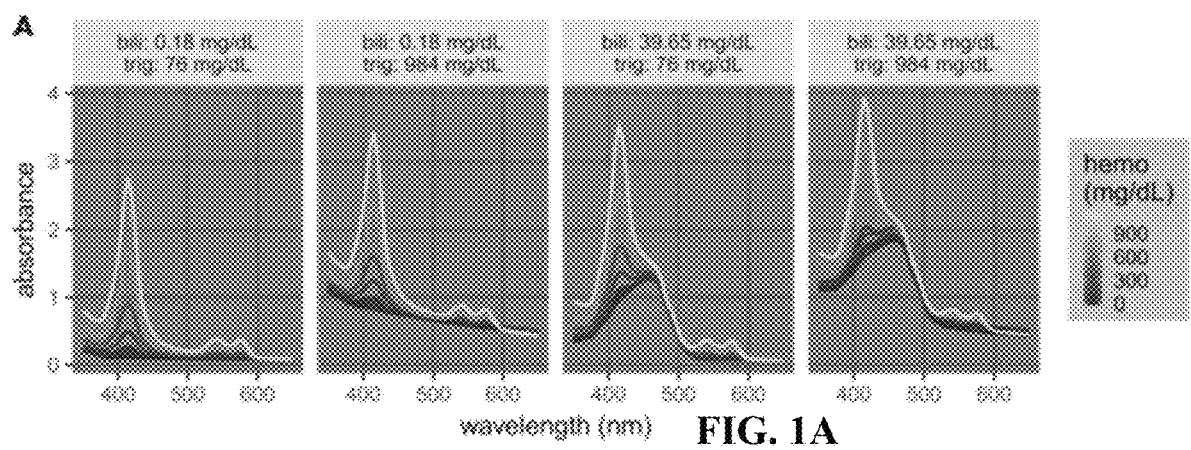
FIG. 1A shows spectra of samples with different concentrations of hemoglobin at low/high permutations of bilirubin and triglycerides as described herein.
Figure 1B:
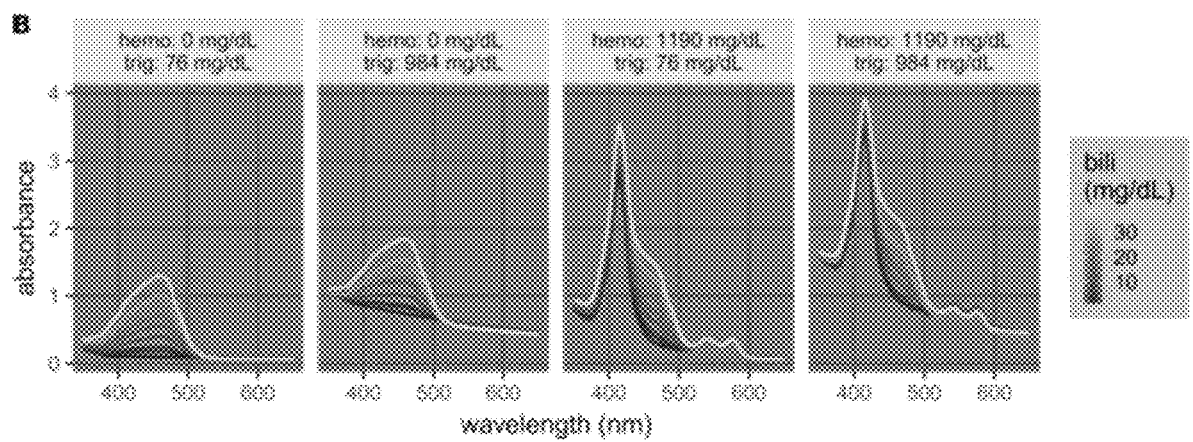
FIG. 1B shows spectra of samples with different concentrations of bilirubin at low/high permutations of hemoglobin and triglycerides as described herein.
Figure 2:
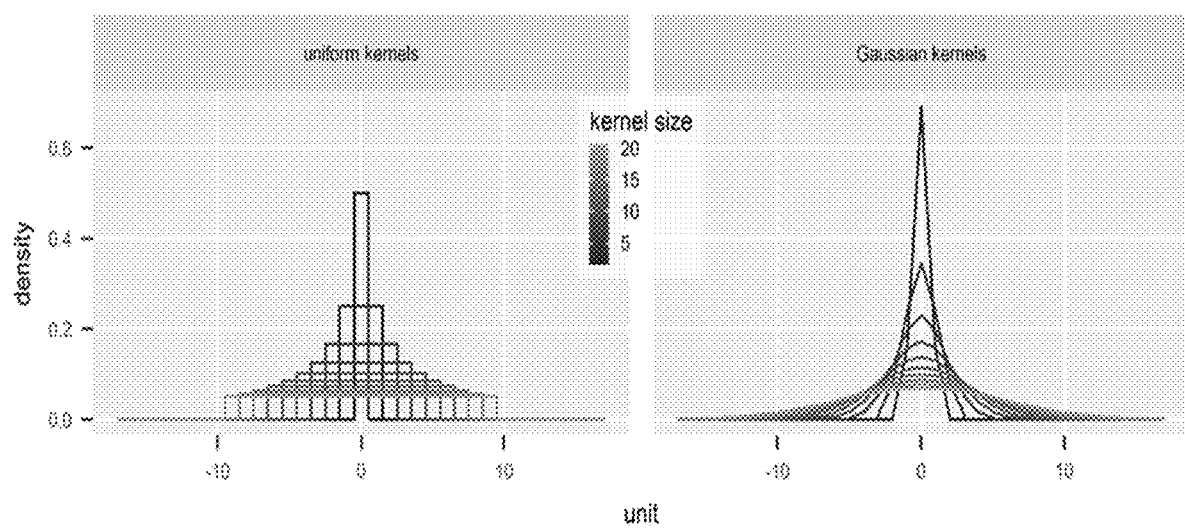
FIG. 2 shows examples of uniform kernels and Gaussian kernels for use with the embodiment herein.

Hemolysis, icterus, and lipemia are indicated by different features in the absorption spectra that may interfere with one another. Hemolysis is caused by the lysis of blood cells before the cell/supernatant separation to obtain plasma or serum, and hemolysis is quantified by the concentration of hemoglobin, which absorbs at 340 mm to 440 nm and 540 nm to 580 nm (FIG. 1A). Icterus is the interference caused by bilirubin, which absorbs light with a broad peak around 460 nm that strongly interferes with the major hemoglobin peak at 415 nm (FIG. 1B). Lipemia is the interference caused by lipid particles, which scatter light and lead to an apparent absorption across a wide range of the ultraviolet/visible spectrum (400 nm to 800+ nm). Due to their proximity, the hemoglobin and bilirubin peaks partially overlap with each other, and the apparent absorption by triglycerides affects the whole spectrum (FIGS. 1-2). Many commercial clinical analyzers utilize absorbance values at wavelengths from 340 nm to 800 nm and complicated calibration procedures to account for this issue.

Background Subtraction in the Detection/Quantification of Hemolysis and Icterus:

Calculation of Background-Subtracted Spectra

For at least one non-limiting example herein to avoid interfering signals, true signals near or at spectral peaks of interest can be obtained by way of background subtraction. In each measurement of this non-limiting example, the background spectrum is calculated by convoluting the raw spectrum (also known as original spectrum and major spectrum) with a kernel, and the background-subtracted spectrum is the difference between the raw spectrum and the background. The types of kernels include, but are not limited to, uniform distributions, Gaussian distributions, or other suitable distributions. Other kernels can be adapted for use with the embodiments herein.

In this embodiment, the size of a uniform kernel is defined as the width of the range of positive density, while the size of a Gaussian kernel is defined as the corresponding standard deviation divided by $\sqrt{1/12}$, so that kernels of different types but of the same size have the same standard deviation. The convolution using a uniform kernel is equivalent to the application of a mean filter; and the convolution using a Gaussian kernel is equivalent to the application of a Gaussian filter (for example, a low-pass filter). Other filters that are used for smoothing may be used to calculate the background as well.

FIG. 2 shows examples of uniform kernels and Gaussian kernels for use with the embodiment herein. The plots show the probability density functions of the kernels of the specified types (Gaussian or uniform) and sizes (2-20). The functions are centered at 0. For each uniform kernel, the width of the non-zero range is defined as the size. For each Gaussian kernel, the standard deviation is defined as the size multiplied by $\sqrt{1/12}$ (to match the standard deviation of a uniform kernel of the same size). Note that only values at integer x-positions are plotted because the kernels are discretized to be convoluted with discretized signals.

Background-Subtraction for Hemolysis Detection/Quantification

Figure 3:
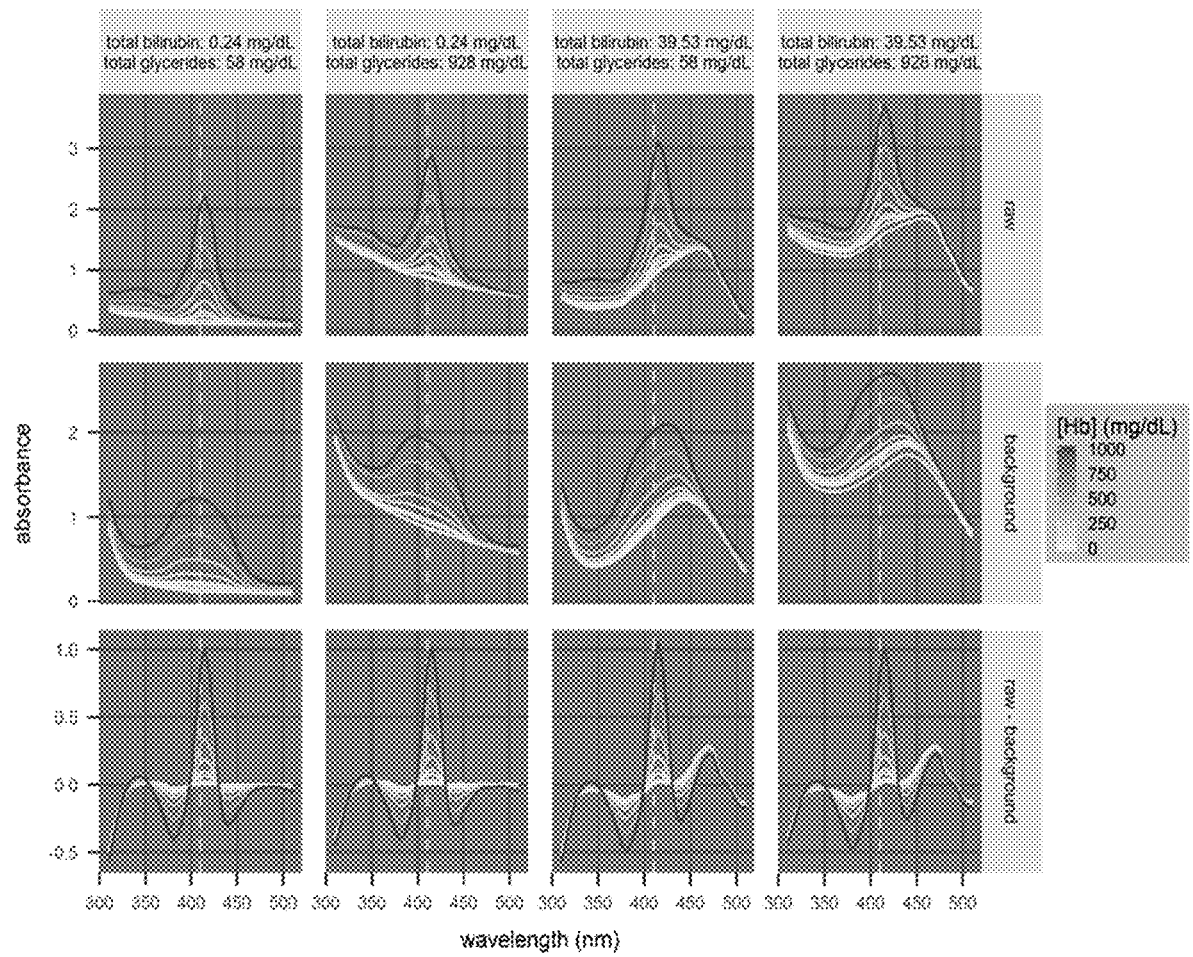
FIG. 3 shows the use of background-subtracted spectra to reduce spectral interference according to at least one embodiment herein.

In another non-limiting example, background-subtracted spectra can be utilized for the quantification/detection of hemolysis. This idea is demonstrated by the analysis of samples at different levels of hemolysis ([Hb] of 0, 20, 60, 80, 180, 340, and 1000 mg/dL) at different combinations of low and high levels of icterus (0.24 or 39.53 mg/dL total bilirubin) and lipemia (58 or 928 mg/dL total glycerides). Without the background subtraction step, the raw absorption spectra contains unexpected signals from icterus and lipemia, and the peaks at 415 nm are elevated unexpectedly as seen in FIG. 3. Background-subtracted spectra with different levels of icterus and lipemia are similar in the region of interest. For example, with the uniform kernel of size 14 (1 unit=5 nm), the background-subtracted absorbance values at 410 nm at different hemolysis levels are similar in all interference conditions tested, and are not dependent on the levels of icterus and/or lipemia.

As seen in FIG. 3, an example is shown using background-subtracted spectra used for the detection/quantification of hemolysis (via [Hb]). The plots show raw, background, and background-subtracted (raw-minus-background) spectra of samples at different hemolysis levels ([Hb] of 0, 20, 60, 80, 180, 340, and 1000 mg/dL) at combinations of low and high icterus and lipemia (total bilirubin=0.24 or 39.53 mg/dL; total glycerides=58 or 928 mg/dL). The dashed line at 410 nm indicates the wavelength where the background-subtracted signals are independent of icterus and lipemia levels, and can be used to quantify [Hb]. The raw spectra were collected at wavelengths that are multiples of 5 nm. The background spectra were calculated by convoluting the raw spectra with a uniform kernel of size 14 (1 unit=5 nm) (FIG. 2).

Kernel Optimization

Overall, the technique of background subtraction can be used to detect/quantify hemolysis or icterus in the presence of different levels of the other types of interference. It should be understood in some embodiments that the relevant wavelengths to obtain background-subtracted signals do not necessarily have to be at the peak of the substances of interest (e.g. 415 nm for hemoglobin or 460 nm for bilirubin), and the background-subtracted signals are not necessarily non-negative. The kernels used to demonstrate the idea (size-14 uniform kernel for hemolysis, and size-18 uniform kernel for icterus) were chosen from different options (FIG. 2) to minimize the p-value of the t test to distinguish 2 lowest levels of the interference of interest in the presence of all combinations of other types of interference (Table 1).

It should be understood that, by way of non-limiting example, at least two new methods described herein (FIG. 3A) can be intended to eliminate interfering signals and obtain clean spectral signals that enable the quantification of one interferent (hemolysis or icterus) in the presence of various amounts of others. While they are both based on the geometry of the spectra, the details are different.

Figure 3A:
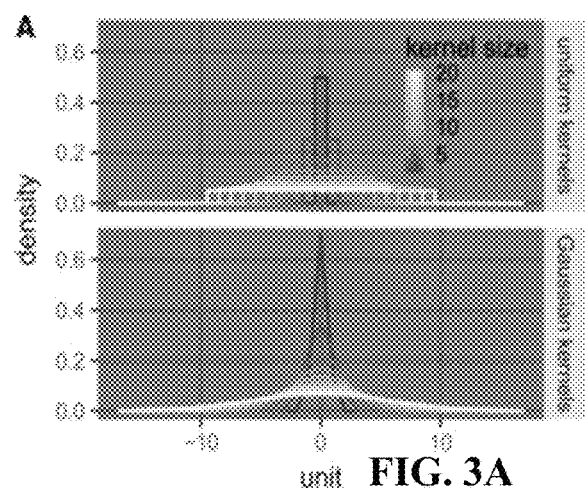
FIGS. 3A-3B show embodiments of methods of background subtraction as described herein.
Figure 3B:
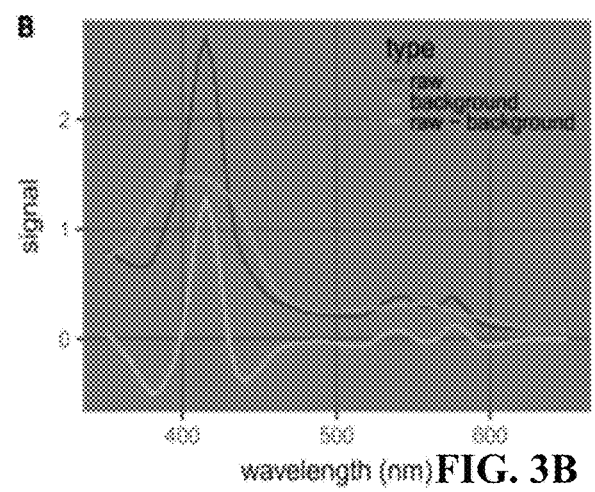
Figure 3C:
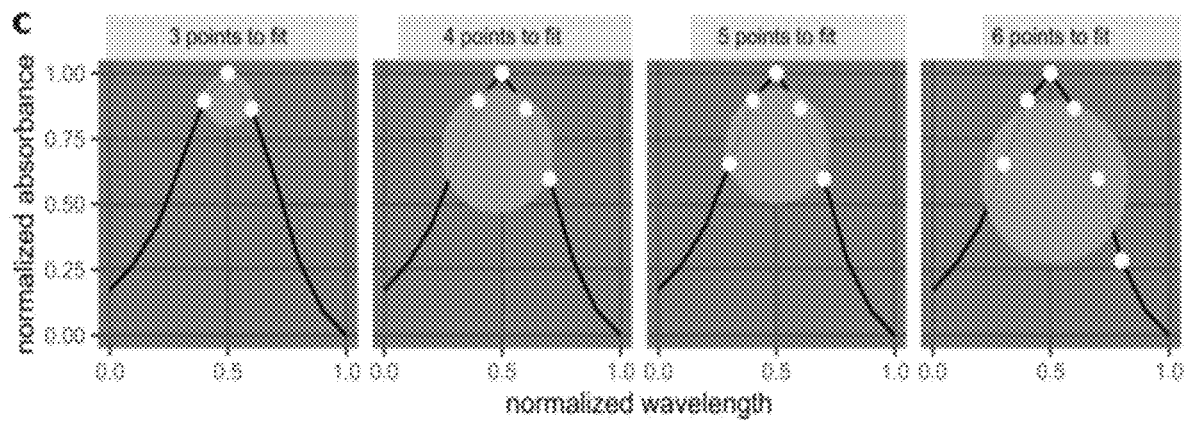
FIG. 3C shows an embodiment of curvature calculation as described herein.

By way of non-limiting example, explanation of the methods of background subtraction (FIGS. 3A, 3B) and curvature calculation (FIG. 3C). For at least one embodiment herein, FIG. 3A shows plots of possible kernels used for the convolution to calculate the background spectra, which are probability density functions of uniform distributions and Gaussian distributions. The kernel size of a certain distribution function is defined as its standard deviation multiplied by the square root of 12, which is the range of the distribution if it is uniform. An optimization step may be used to choose an appropriate method specified by the kernel and the wavelength used to obtain the final values. B) Plots showing example "raw," "background," and "raw-background" spectra of a sample. The background spectrum was calculated with a uniform kernel of size 14 (14 points*5 nm/points=70 nm). C) Plots illustrating curvature calculation. At a certain wavelength (at or near a peak), a certain number of points are used for fitting a circle going through them by minimizing a cost function (Eq. 1). The resulting curvature is the inverse of the radius of such circle. To display the circles with clarity, the wavelength and the absorbance were normalized in these plots, while the actual calculations were done with the original values. An optimization step may be done to choose a curvature calculation method specified by a certain wavelength and number of points used for fitting.

By way of non-limiting example, the first method takes inspiration from background subtraction techniques used in image processing and is more general than those previously employed. The processed signal is called the background-subtracted signal. It is obtained by convoluting the raw signal with a blurring kernel to calculate the background (FIG. 3A), and subsequently, subtracting the background from the raw signal (FIG. 3B). Optionally, the second method is derived from the empirical observation that the shapes of the peaks generally do not depend on the background. In this case, we took the processed signal as the spectral curvature near or at the peak of interest, which is the inverse of the radius of the circle fitted through spectral points (FIG. 3C). Derivatives, which also provide shape information, have previously been employed to detect and measure hemolysis and icterus. Herein, the curvature, which can be calculated using the first and second derivatives, provides a direct description of the shape of the curve near or at a particular peak.

The methods were evaluated with 510 samples containing permutations of levels of hemolysis, icterus, and lipemia, as specified by the concentrations of hemoglobin, bilirubin, and triglycerides, respectively (Table 1). We used this sample set to explain the two new methods described herein and demonstrate their performance in comparison to traditional methods.

TABLE 1

| Level Hemolysis: | hemoglobin (mg/dL) | Icterus:bilirubin (mg/dL) | Lipemia:triglycerides (mg/dL) |
|---|---|---|---|
| 0 | 0 | 0.18 | 76 |
| 1 | 30 | 2.76 | 127 |
| 2 | 50 | 4.77 | 175 |
| 3 | 70 | 9.62 | 215 |
| 4 | 180 | 14.63 | 275 |
| 5 | 370 | 19.20 | 462 |
| 6 | 760 | 29.67 | 740 |
| 7 | 1190 | 39.65 | 984 |

Performance in Many Samples

Figure 3D:
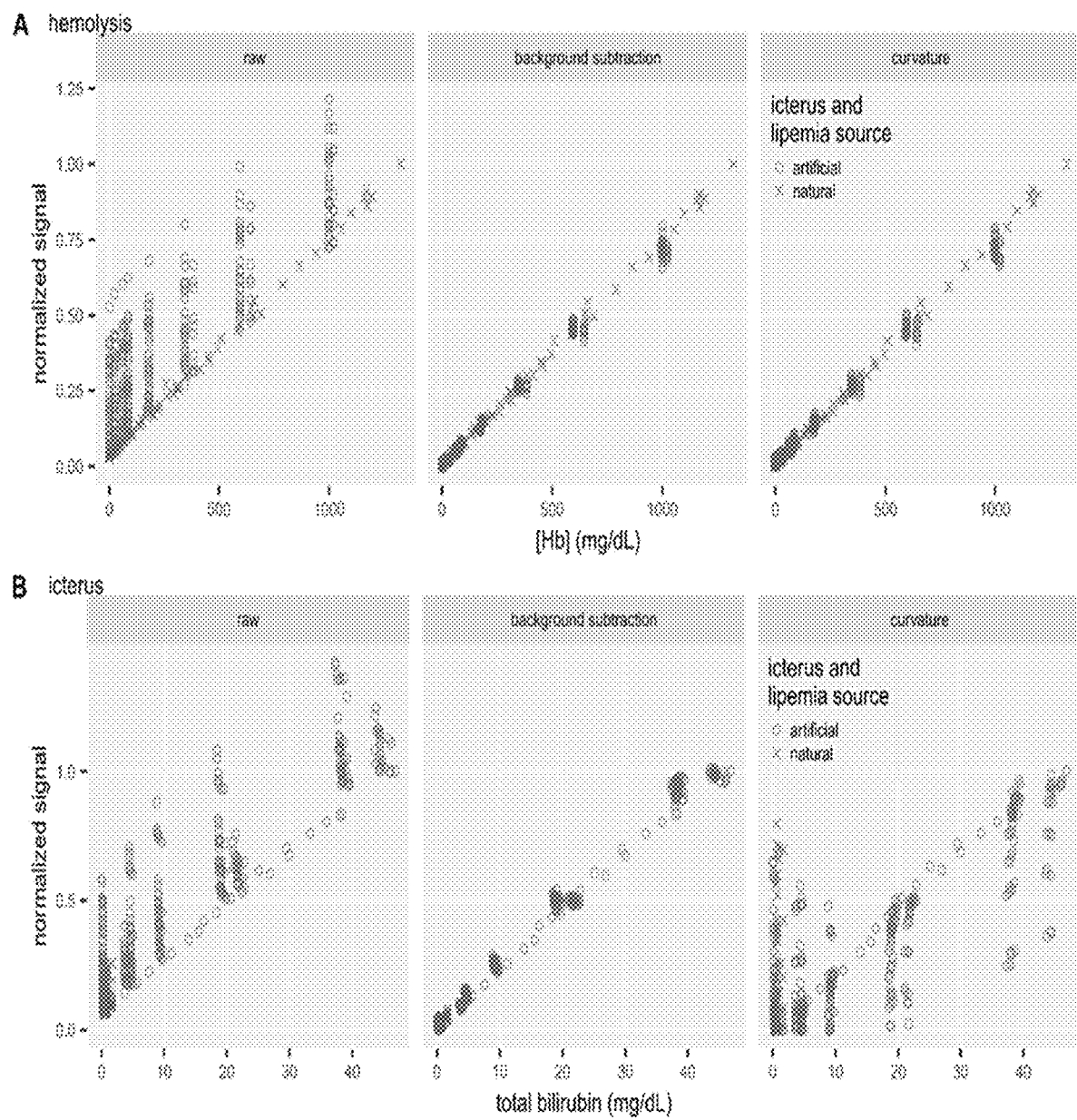
FIG. 3D shows the use of background subtraction and curvature removing interference signals for the detection/quantification of hemolysis (A) and icterus (B) according to at least one embodiment herein.

The methods based on curvature calculation and background subtraction were applied to hundreds of samples, which include those with different combinations of hemolysis/icterus/lipemia combinations and those collected less systematically as seen in FIG. 3D. The source of hemolysis interference was natural in all samples because the hemolysate solutions were obtained from blood cells lysed by freezing/thawing. Naturally occurring icterus and lipemia were of lower levels; therefore, bilirubin and lipid from artificial sources were added into the samples to achieve higher levels of icterus and lipemia. For hemolysis detection/quantification, the raw absorbance values correlate weakly to the expected [Hb], while both the background-subtracted signals and the curvatures correlated very well with the expected [Hb]. For icterus, the background subtraction method performs well, but the curvature method does not. Therefore, the method based on background subtraction is suitable for the detection/quantification of both hemolysis and icterus, while the method based on curvature calculation is only suitable for the detection/quantification of hemolysis.

Referring still to FIG. 3D, the performance is shown of the methods based on background subtraction and curvature calculation in removing interference signals for the detection/quantification of hemolysis (A) and icterus (B). The sample sizes for hemolysis plots and icterus plots are 352 and 392, respectively. The background subtractions for the hemolysis and icterus signals were done using uniform kernels of sizes 14 and 18 (unit=5 nm), respectively (FIG. 2). The curvatures for hemolysis detection/quantification were calculated using absorbance values at 405, 410, 415, 420, and 425 nm. The curvatures for icterus detection/quantification were calculated using absorbance values at 450, 455, 460, 465 and 475 nm. Artificial sources of icterus and lipemia were conjugated bilirubin and Intralipid®, respectively.

Figure 4:
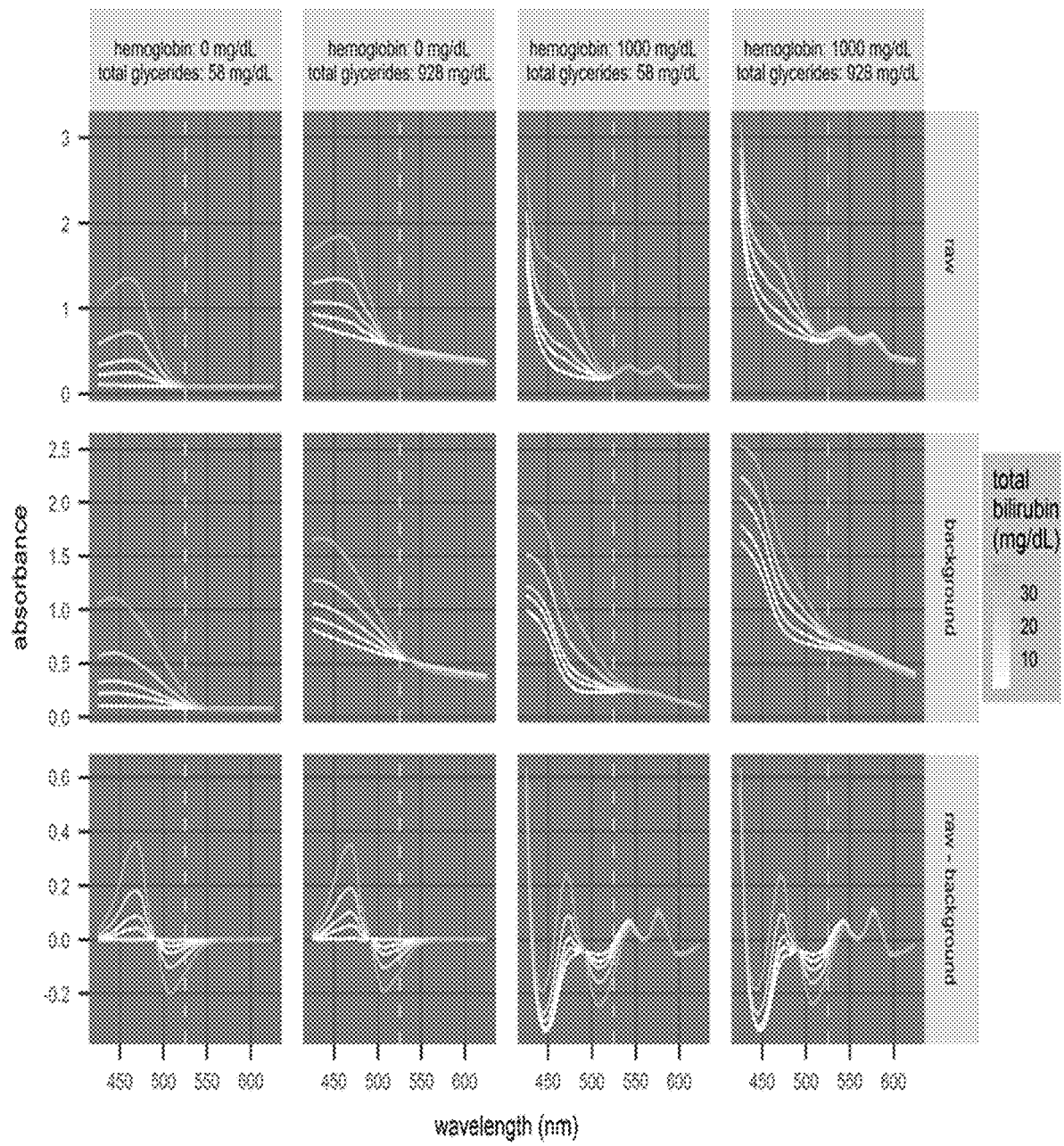
FIG. 4 shows charts of absorbance relative to wavelength according to at least one embodiment herein.

FIG. 4 shows charts of absorbance relative to wavelength according to at least one embodiment herein.

Advantage(s)

For at least some embodiments described herein, they have at least some advantages in comparison to interference correction methods that are based on absorbance values at multiple wavelengths across the UV-Vis range, such as the ones used for hemolysis and icterus detection on traditional instruments.

Firstly, only a short range of wavelengths around the major wavelength of interest is used in most embodiments. This advantage enables simplifications/improvements of the detection instrument, such as but not limited to a smaller required wavelength range of the light source, a smaller required width of the array detector (in a prism/grating-based spectrophotometer), and a higher wavelength resolution (the same array detector real estate can be used for a smaller wavelength range in a prism/grating-based spectrophotometer).

Secondly, a smaller range of samples used for the calibration of a method is required. In at least one embodiment, the processed signals (curvatures or background-subtracted absorbance values) do not depend on the levels of interference types (FIG. 5), so the calibration process does not need information from samples with wide ranges of interference levels. For example, if it is hard to find samples at high icterus levels, only normally icteric samples can be used for the calibration.

Thirdly, embodiments of the methods described here are less susceptible to the presence of unknown interference types. The choice of wavelengths in traditional methods depends on absorption wavelengths of known interference types, while both curvature calculation and background subtraction are mostly agnostic of the interference types and only depend on the absorption of the substance of interest.

Data Processing and Analysis (Signal Calculation)

As part of the calculation of background-subtracted signals, the convolution of the original signals with blurring kernels was performed to obtain the background signals. A specific kernel is a probability density function (PDF) (mean, $\mu=0$; standard deviation, $\sigma$). The size of the kernel is defined as $\sigma\sqrt{12}$ (e.g., the range, in the case of a uniform distribution). Because the spectra were sampled at discrete wavelengths, the kernels were represented as discrete points along the continuous curves (the PDFs) in the calculation. In particular, for each Gaussian kernel, only points in the [$-3\sigma$, $3\sigma$] (rounded) range were used.

The curvature at a specific region of a spectrum is defined as, where is the radius of the circle fitted through the data points in that region. The fitting was done by minimizing the cost function (see Eq. 1 below), where is the number of points used for fitting, is the coordinate (wavelength, absorbance) of point i, and is the coordinate of the center.

Linear Regression

In at least one embodiment described herein, linear regression models were used to evaluate different methods of hemolysis and icterus measurements. In such a model, Y, the quantity of interest (e.g., hemoglobin or bilirubin), is a linear combination of signals from the samples (see Equation 2 below).

$$Y = a_0 + a_1 \text{Signal}_1 + a_2 \text{Signal}_2 + \ldots + a_n \text{Signal}_n$$

The model can be trained (calibrated) using a set of samples with known true Ys. In such a process, the coefficients ($a_i$'s) are varied to minimize the sum of the squared differences between the true Ys and the calculated Ys. The optimized coefficients can then be used to calculate the Ys of the test samples. The signals may be absorbance values at specific wavelengths, differences of absorbance values at two specific wavelengths, the background-subtracted signals, or the curvatures. Models with the newly derived signals were compared with models used in commercial analyzers as described in the literature.

Results (Example Results with Background Subtraction)

Figure 5:
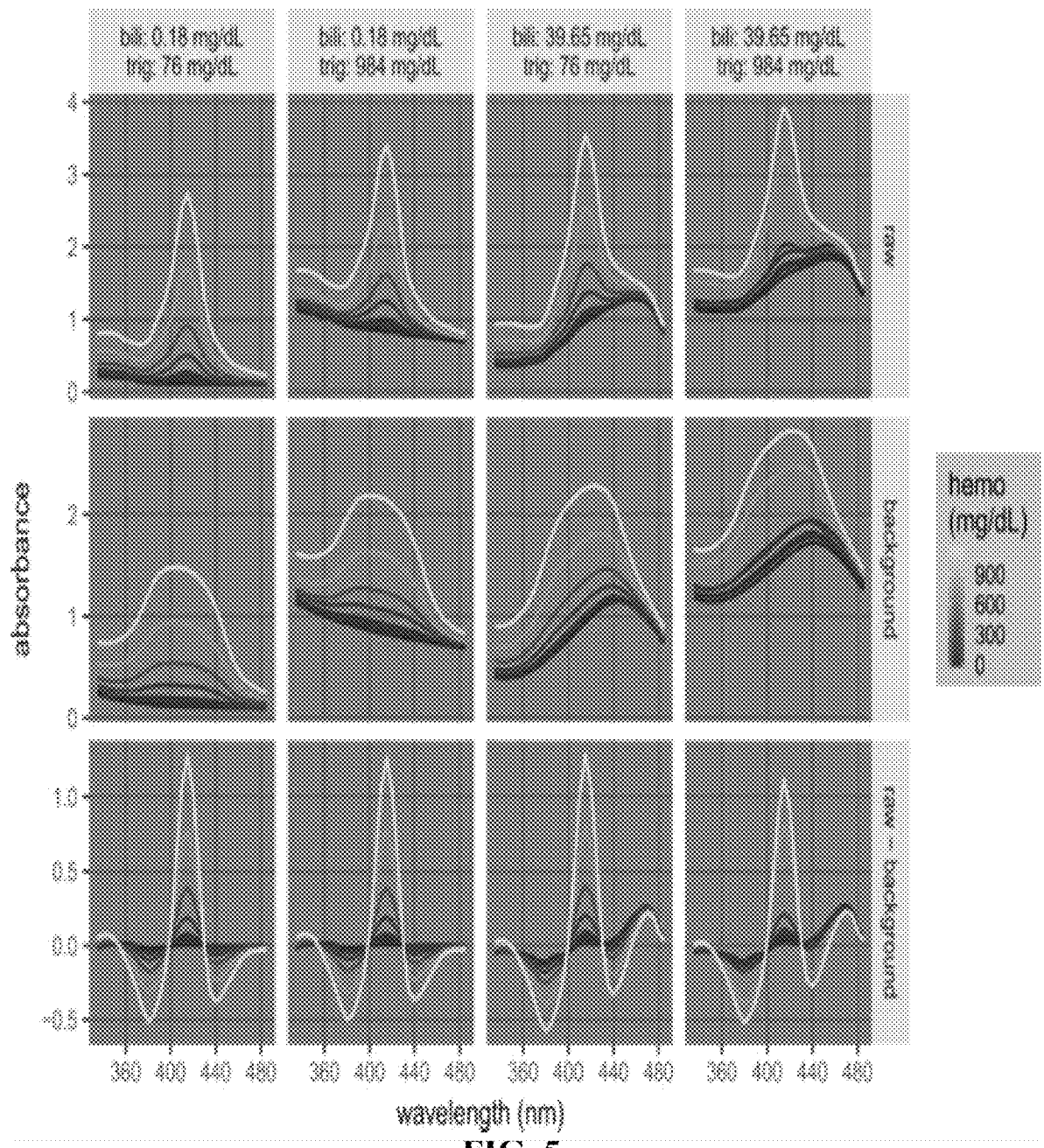
FIG. 5 show background-subtracted spectra used for the quantification of hemolysis according to at least some embodiments as described herein.

In at least one embodiment, it was first tested whether background-subtracted spectra can be utilized for the quantification of hemolysis. The accuracy of this approach was demonstrated by the analysis of samples at various levels of hemolysis (hemoglobin=0, 30, 50, 70, 180, 370, 760, and 1,190 mg/dL) while in the presence of low and high levels of icterus (bilirubin=0.18 and 39.65 mg/dL) and lipemia (triglycerides=76 and 984 mg/dL) (FIG. 5). Without the background subtraction step, the raw absorption spectra contained unwanted signals from icterus and lipemia, and the peaks at 415 nm were elevated. Background-subtracted spectra with different levels of icterus and lipemia were similar in the region of interest. For example, with the uniform kernel of size 14 (1 unit=5 nm), the background-subtracted absorbance values at 420 nm at different hemolysis levels were similar in all interference conditions tested and were not dependent on the levels of icterus and/or lipemia.

By way of non-limiting example, FIG. 5 shows an example background-subtracted spectra used for the quantification of hemolysis. The plots show raw, background, and background-subtracted spectra of samples at different hemolysis levels (hemoglobin [hemo]=0, 30, 50, 70, 180, 370, 760 and 1190 mg/dL) at permutations of low and high icterus and lipemia (bilirubin [bili]=0.18 and 39.65 mg/dL; triglycerides [trig]=76 and 984 mg/dL). The raw spectra were acquired at 5-nm intervals. The background spectra were calculated by convoluting the raw spectra with a uniform kernel of size 14 (or (14−1)*5=65 nm; FIG. 3A).

Figure 6:
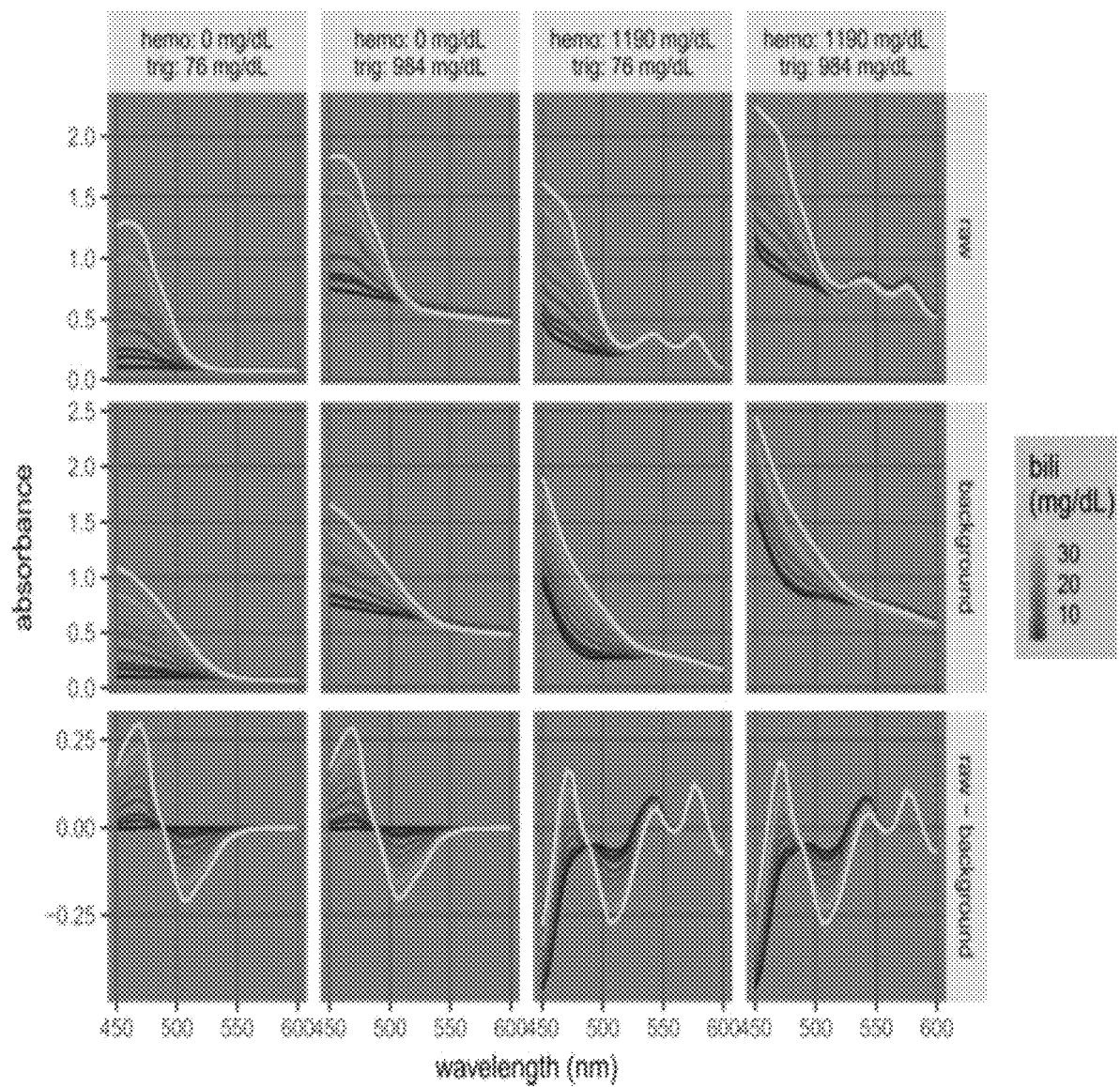
FIG. 6 show background-subtracted spectra used for the quantification of icterus according to at least some embodiments as described herein.

Similarly, background-subtracted spectra can be utilized for the quantification of icterus (FIG. 6). The bilirubin concentrations were 0.18, 2.76, 4.77, 9.62, 14.63, 19.20, 29.67, and 39.65 mg/dL; the hemoglobin concentrations were 0 and 1,190 mg/dL; and the triglyceride concentrations were 76 and 984 mg/dL. While the raw spectra were significantly affected by hemolysis or lipemia, the background-subtracted spectra were similar in all interference permutations tested. In particular, with the uniform kernel of size 17 (1 unit=5 nm), the background-subtracted absorbance values at 525 nm were not affected by the levels of hemolysis and/or lipemia.

FIG. 6 shows example background-subtracted spectra used for the quantification of icterus. The plots show raw, background, and background-subtracted (raw-minus-background) spectra of samples at different icterus levels (bilirubin [bili]=0.18, 2.76, 4.77, 9.62, 14.63, 19.20, 29.67, and 39.65 mg/dL) at permutations of low and high hemolysis and lipemia (hemoglobin [hemo]=0 and 1,190 mg/dL; triglycerides [trig]=76 and 984 mg/dL). The raw spectra were acquired at 5-nm intervals. The background spectra were calculated by convoluting the raw spectra with a uniform kernel of size 17 (or (17−1)*5=80 nm; FIG. 3A).

Example Results with Curvature Calculation

Figure 7A:
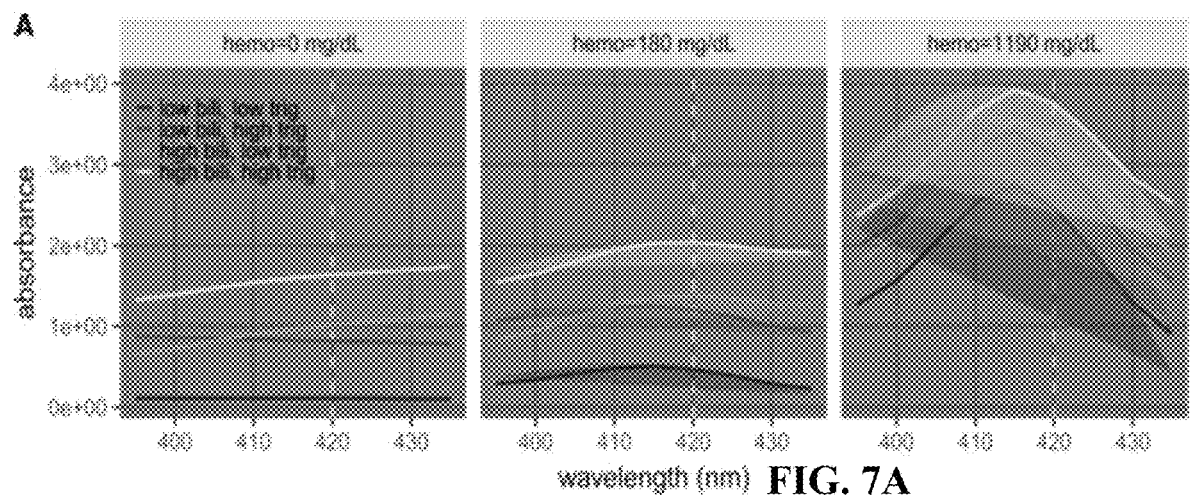
FIGS. 7A-7B show example results of using curvature calculation to quantify hemolysis according to at least some embodiments as described herein.
Figure 7B:
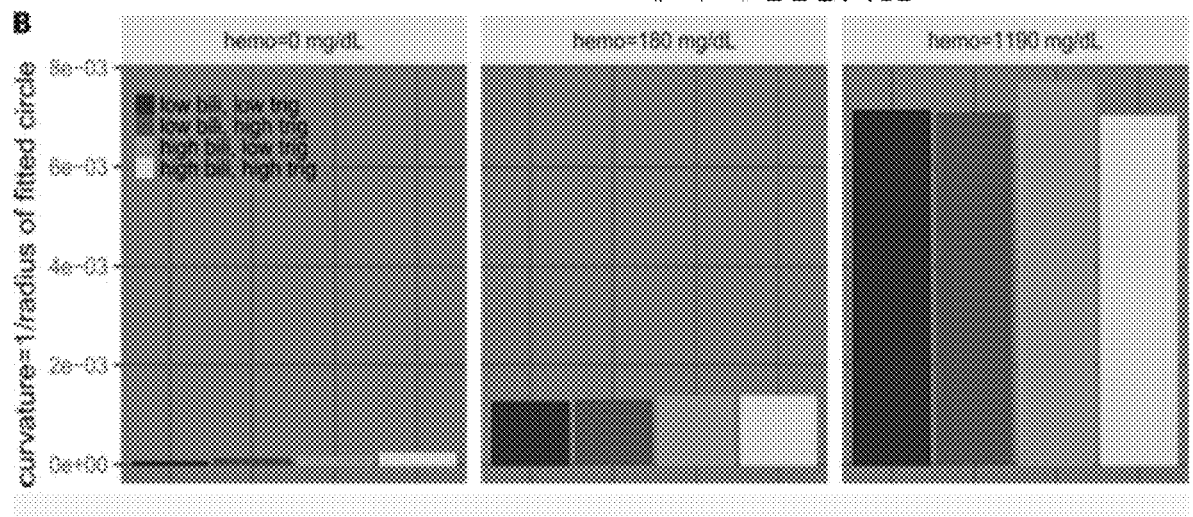

Referring now to FIGS. 7A-7B, in at least one embodiment herein, it was observed that the shape of a specific absorption peak (e.g., the 415-nm hemoglobin peak) did not change if there was interference by a nearby peak (e.g., the 460-nm bilirubin peak) or by an increase in absorption across a wide range of wavelengths (e.g., in the case of lipemia). This was demonstrated with samples having different hemolysis levels (hemoglobin=0, 180, or 1,190 mg/dL) and different permutations of low/high levels of icterus (bilirubin=0.18 and 39.65 mg/dL) and lipemia (triglycerides=76 and 984 mg/dL). At each hemolysis level, samples with different icterus and lipemia levels were found to have markedly different absorbance values (FIG. 7A). Circles were fitted to points near the peaks (at 415, 420, 425, and 430 nm) using least-squares regression with the cost function defined in Eq. 1 (FIG. 7A). The resulting curvatures (the inverses of the radii), which were used as metrics to quantitatively describe the shapes of the peaks, were similar for each group of samples at each hemolysis level, regardless of icterus and lipemia levels (FIG. 7B). This result demonstrates the possibility of using the curvatures to quantify and detect hemolysis.

FIGS. 7A-7B show example results of using curvature calculation to quantify hemolysis. FIG. 7A shows plots showing spectra of samples with three different hemoglobin concentrations (0, 180, 1,190 mg/dL) in separate sub-panels. Each sub-panel shows spectra of samples at low/high permutations of icterus (bilirubin [bili]=0.18 and 39.65 mg/dL) and lipemia (triglycerides [trig]=76 and 984 mg/dL). The dashed lines indicate 420 nm. The shaded circular sectors indicate fitted results using four data points around 420 nm (415, 420, 425, and 430 nm). FIG. 7B shows bar charts showing curvatures calculated from results shown in FIG. 7A.

Figures 8A, 8B:
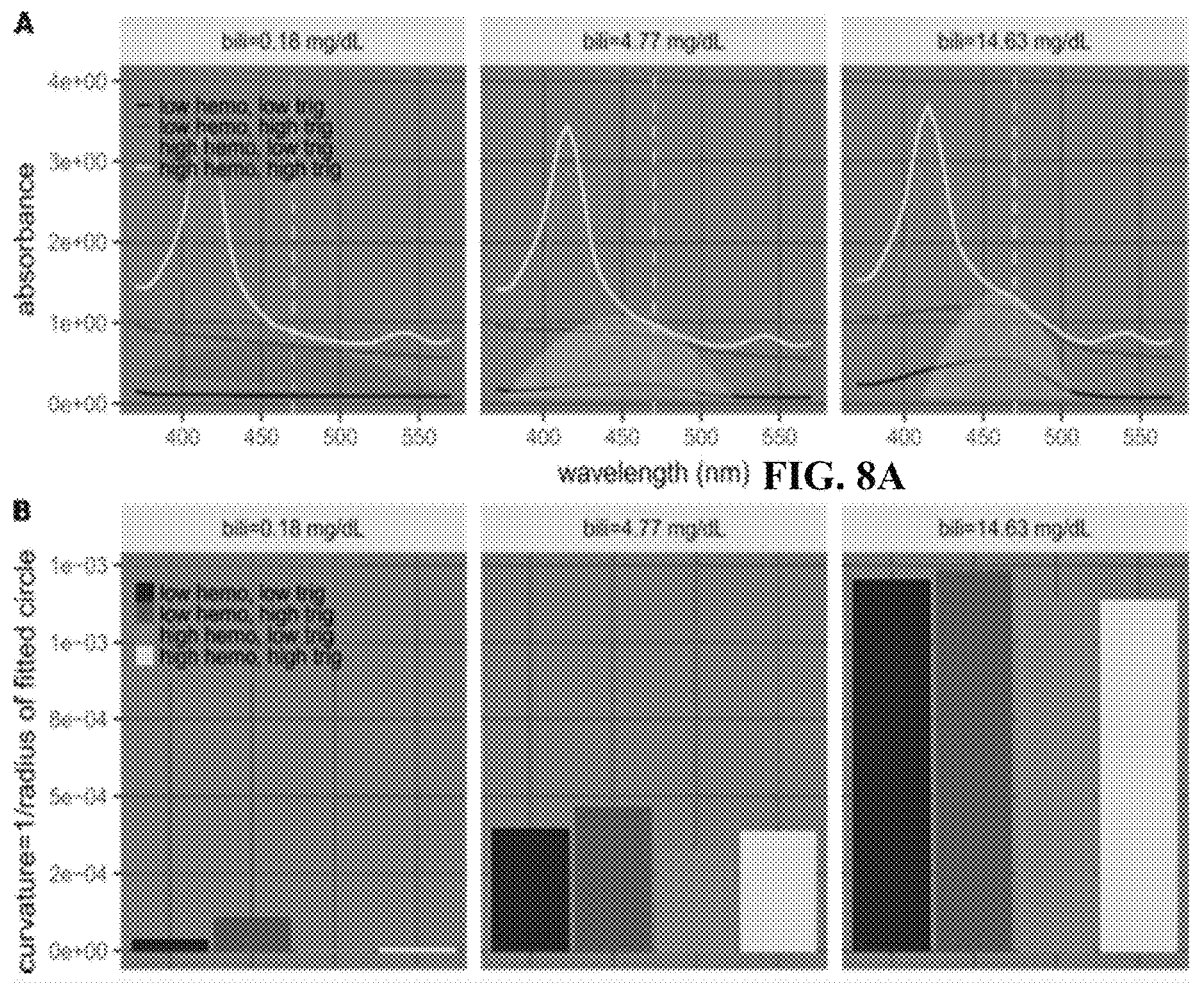
FIGS. 8A-8B show example results of using curvature calculation to quantify icterus according to at least some embodiments as described herein.

This method was also applied to icterus detection and quantification. Similar to the case of hemolysis (FIG. 7A-7B), samples at three different levels of icterus (bilirubin=0.18, 4.77, and 14.63 mg/dL) and different low/high permutations of hemolysis (hemoglobin=0 and 1,190 mg/dL) and lipemia (triglycerides=76 and 984 mg/dL) were used to demonstrate feasibility (FIGS. 8A-8B). At each icterus level, samples with different hemolysis and lipemia levels were found to have markedly different absorbance values (FIG. 8A). Circles were fitted to data points near the peaks (at 465, 470, 475, and 480 nm) using least-squares regression with the cost function defined in Eq. 1 (FIG. 8A). The resulting curvatures (the inverses of the radii), which we used as metrics to quantitatively describe the shapes of the peaks, turned out to be similar for each group of samples at each hemolysis level, regardless of icterus and lipemia levels (FIG. 8B).

By way of non-limiting example, FIGS. 8A-8B show example results of using curvature calculation to quantify icterus. FIG. 8A shows plots showing spectra of samples with three different bilirubin (bili) concentrations (0.18, 4.77, 14.63 mg/dL) in separate sub-panels. Each sub-panel shows spectra of samples at low/high permutations of hemolysis (hemoglobin [hemo]=0 and 1190 mg/dL) and lipemia (triglycerides [trig]=76 and 984 mg/dL). The dashed lines indicate 470 nm. The part-circles indicate fitted results using four data points around 470 nm (465, 470, 475, and 480 nm). FIG. 8B shows bar charts showing curvatures calculated from results shown in FIG. 8A.

Optimization of Parameters

There are multiple options to consider when applying the new methods described herein. The background calculation step can be done with different kernels of different types and sizes and requires specification of the wavelength of interest to obtain the processed signal. The curvature calculation can be done with different choices for the center wavelength and a different number of points around each chosen center wavelength. In addition, there are multiple metrics to evaluate different implementations, and we considered two metrics herein.

The first metric is the R2 obtained from fitting the reference concentrations with the calculated signals. The second is the p-value of the Welch's t-test performed on two groups of samples of the lowest and second lowest levels, which is motivated by the possible need for very sensitive detection in some applications. For practicality, $-\log 10(p)$ values were used instead of pvalues. Note that the Welch's t-test was chosen over the student's t-test because the variances at different levels are not expected to be the same.

In at least one embodiment, an optimization step was performed to determine the optimal parameters for each method (background subtraction or curvature calculation) for each interferent (hemolysis or icterus). In particular, the center wavelength was varied from 350 nm to 650 nm (with steps of 5 nm). For background calculation, the kernel types were 1) Gaussian and 2) uniform, while the size was varied from 2 to 20 units (1 unit=5 nm). For the curvature calculation, the number of points was varied from three to 16. At a certain center wavelength, if the number of points was even, more points were chosen on the side of larger wavelengths. Metrics of R2 and $-\log 10(p)$ for all cases were calculated. Only points with good overall performance ($R \geq 0.95$ and $p \leq 0.05 \Leftrightarrow -\log 10(p) \geq 1.3$) were plotted (FIG. 9). The metric $-\log 10(p)$ was chosen because of its usefulness; if a method has a high $-\log 10(p)$, it also has a high R2, while the converse is not true.

Comparison:

By way of non-limiting example, the performance was compared of each of the optimized methods (Table 2) to those of traditional methods currently used in conventional chemical analyzers [1, 3, 20] using linear regression models. Each model (Table 3, Eq. 2) was evaluated by 10 iterations at each training fraction. In each iteration, the sample set (Table 1) was randomly split into training and testing sets, with the training fraction specifying the ratio of the number of samples in the training set versus the total number of samples. The metric calculated from each iteration was the same as the metric used to optimize the new methods (FIG. 9), which is the $-\log 10(p)$ value obtained from the Welch's t-test performed on two groups of samples of the lowest and second lowest interferent levels. The $-\log 10(p)$ values were averaged over the iterations. The results for both hemolysis and icterus showed that the background-subtracted signals and the curvatures performed better than most other models that involve multiple absorbance values (Table 3). In particular, models that use either background-subtracted signals or curvatures were in the top three for both hemolysis and icterus detection.

Table 2 shows parameter search results for hemolysis and icterus detection using background subtraction and curvature calculation, in comparison to the raw signals (raw absorbance values). The selected parameters are those that provided the highest $-\log 10(p)$.

TABLE 2

|  | Hemolysis | Icterus |
| --- | --- | --- |
| Raw signal | 415 nm (raw absorbance values) | 460 nm (raw absorbance values) |
| Background-subtracted signal | 410 nm size-14 uniform kernel | 525 nm size-17 uniform kernel |
| Curvature | 4 points about 420 nm | 4 points about 470 nm |

Advantages of the New Methods

The two methods described herein have three major practical advantages versus interference correction methods that are based on absorbance values at multiple wavelengths across the ultraviolet/visible range, such as those used for hemolysis and icterus detection on many commercial analyzers. First, the methods described herein are less susceptible to the presence of unknown interferents. The choice of wavelengths in traditional methods depends on absorption wavelengths of known interferents, while both curvature calculation and background subtraction are mostly agnostic of the interferents and only depend on the absorption of the substance of interest. Even though the optimized hemolysis and icterus signals slightly deviated from the peaks (415 nm for hemolysis and 460 nm for icterus) (Table 2), the signals at the peaks would still provide good performance, with p-values distinguishing the two lowest interference levels (of hemolysis or icterus) much lower than 0.05 (i.e., $-\log 10(p)$ values much larger than 1.3).

Second, traditional methods require calibration using samples with wide ranges of interference levels, while the methods using background-subtracted signals or curvatures do not. We performed an example analysis to demonstrate this notion. Using only samples with a maximum interference level of 1 (Table 1) to calibrate regression models, it was calculated the corresponding hemoglobin and bilirubin values for all 510 samples. In the eight samples used for these calibration steps, the highest hemoglobin (30 mg/dL), bilirubin (2.76 mg/dL), and triglyceride (127 mg/dL) levels were practically low. Traditional methods gave large biases and poor correlations, while those using background-subtracted signals and curvatures gave good agreement. As expected, with $-\log 10(p)$ as the metric, the maximum level of interference used for calibration had to be increased for the performance of traditional methods to improve. In contrast, the methods using background-subtracted signals or curvatures performed very well, even when a maximum level of 1 is used for calibration. The independence of the methods involving background-subtracted signals and curvatures allows the calibration to be done even with samples of limited interference levels (e.g., those naturally collected instead of those made via a comprehensive procedure like the samples used for this work).

Background-subtracted signals require ranges spanning 65 nm for hemolysis and 80 nm for icterus, which are ranked in the middle in both cases. This advantage enables possible simplifications and improvements of the detection instrument, such as a smaller wavelength range of the light source, a smaller required width of the array detector (in a prism/gratingbased spectrophotometer), and a higher wavelength resolution (due to a smaller wavelength range for the same detector size). While typical commercial analyzers have full-scale spectrophotometers, point-of-care devices may benefit from this advantage.

Discussion

By way of non-limiting example, one approach of the two new methods described herein (those involving background-subtracted signals and curvatures) is to obtain clean spectral signals even with interference. Therefore, their application can be extended to other spectral measurements. For example, many clinical assays with optical readouts based on absorption spectra employ multiple-wavelength readings to subtract out interfering signals and require the knowledge of possible interferents. The two new methods described can be readily applied to those assays, with the practical advantages described above.

It is worth noting that the background-subtracted signals may be negative at certain points in the parameter space (as specified by the wavelength, kernel type, and kernel size) (FIGS. 5-6). A negative signal may occur at a wavelength next to a peak or at a peak near another one that is much higher. At first glance, it may not seem intuitive to use such negative signals, but they do contain information about the peaks of interest. Indeed, the optimal background-subtracted signal for icterus measurements (Table 3) was negative (FIG. 6) but still performed well.

TABLE 3

| Model name | Interferent | Signals (absorbance values or other types) |
|---|---|---|
| CLSI 1 | Hemolysis | 405/700 |
| CLSI 1 | Icterus | 452/700 |
| CLSI 2 | Hemolysis | 571/596 |
| CLSI 2 | Icterus | 478/505 |
| CLSI 3 | Hemolysis | 572/604 628/660 |
| CLSI 3 | Icterus | 500/524 572/604 628/660 |
| CLSI 4 | Hemolysis | 522/750 |
| CLSI 4 | Icterus | 507/776 |
| CLSI 5 | Hemolysis | 410/480 600/800 |
| CLSI 5 | Icterus | 480/570 600/800 |
| CLSI 6 | Hemolysis | 340 410 470 600 670 |
| CLSI 6 | Icterus | 340 410 470 600 670 |
| CLSI 7 | Hemolysis | 570/600 |
| CLSI 7 | Icterus | 480/505 |
| Farrell2016_5 | Hemolysis | 583/629 |
| Farrell2016_5 | Icterus | 480/512 |
| Bg-sub signal (Table 2) | Hemolysis | 410 nm size-14 uniform kernel |
| Bg-sub signal (Table 2) | Icterus | 525 nm size-17 uniform kernel |
| Curvature (Table 2) | Hemolysis | 4 points about 420 nm |
| Curvature (Table 2) | Icterus | 4 points about 470 nm |
| Raw | Hemolysis | 415 |
| Raw | Icterus | 460 |

Figure 9A:
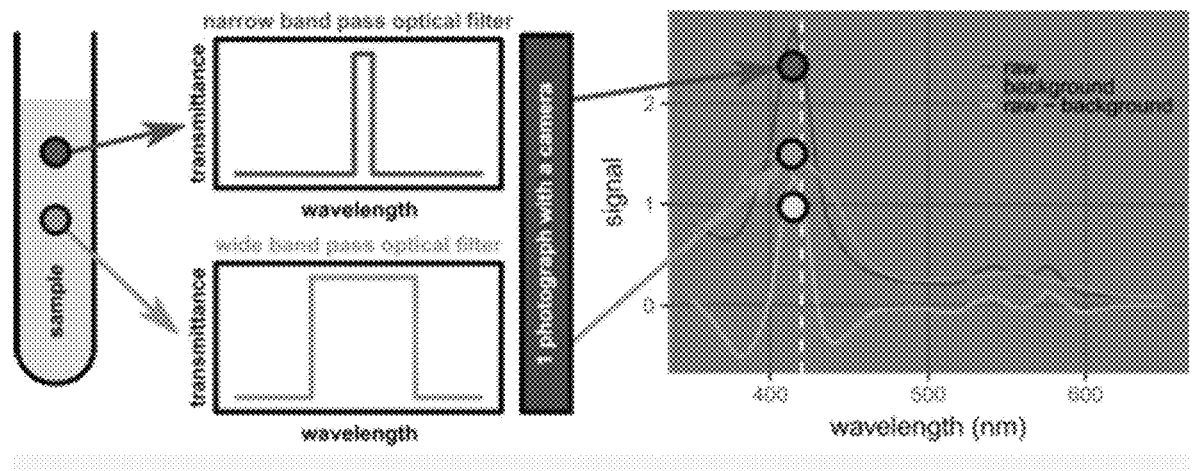
FIG. 9A shows a method of using photography to acquire background-subtracted signals with a narrow band pass optical filter and a wide band optical filter according to at least one embodiment as described herein.

In some settings, such as when hemolysis detection is required at the collection site, the use of an inexpensive and simple device to collect spectral data is desirable. The background subtraction method described herein can potentially enable such data acquisition to be done with a simple camera. The novelty is that the background subtraction method only requires two optical filters, one with a narrow band to obtain the major signal, and the other one with a wider band to obtain the background signal (FIG. 9A). If the two optical filters are placed in the region of interest side-by-side in the same field of view, only one image is needed to obtain the background-subtracted signal for each sample. Such a design would be compatible with resource-limited settings. For example, to detect hemolysis at the collection site without a spectrophotometer, one could photograph the plasma fractions of centrifuged collection devices using a simple point-and-shoot camera (or a cell phone camera) with the light path that includes a hybrid filter, which is composed of a narrow-band pass region and a wide-band pass region (e.g., 5-nm and 65-nm wide filters for hemolysis measurements). There have been efforts to develop technologies to detect hemolysis at the collection site such as one involving the use of color intensities of images taken with a camera. The method proposed herein would have a much smaller and simpler sample set for calibration and provide performance similar to that of a spectrophotometer, thus avoiding the need to deal with the complex, nontrivial conversion of the absorption/scattering spectra to recorded colors.

By way of non-limiting example, The new methods described in this paper, which are based on background-subtraction and curvature calculation, provide the ability to quantify and detect hemolysis and icterus with several practical advantages: 1) better robustness in terms of eliminating signals from unwanted substances, some of which may not be known beforehand, 2) smaller sets of samples used for calibration with few levels of interference, and 3) simpler instruments (spectrophotometers with smaller detectors/short wavelength ranges or cameras equipped with pairs of filters). These new methods do not have advantages over traditional methods with respect to the number of discrete wavelengths required. A camera-based implementation would require further hardware engineering, and the implementation of these new methods, in general, may involve other methods of performing background-subtraction (e.g., those with other blurring methods) or curvature calculation (e.g., those using methods other than circle fitting). Such implementation could benefit cases of sample collection in resource-limited settings. For example, in remote sites where samples are collected and sent to centralized laboratories, the ability to detect interference at the point of collection would allow for immediate re-drawing. Furthermore, if the hardware is adapted to work with small-volume samples (e.g., those collected by fingersticks), it would be possible to integrate the methods described herein with point-of-care diagnostic instruments and contribute to the effort of bringing diagnostics to developing countries or other under-served settings. Overall, these new data analysis methods can enable new practical possibilities in the development of interference screening methods.

OTHER EMBODIMENTS

Applications in Other Spectral Measurements

For at least one non-limiting example, the utility of the two methods described above is to obtain clean signals in the presence of interference in spectra. Optionally, their application can be extended to other spectral measurements. For example, currently, the background subtraction step using single background wavelengths is part of some clinical chemistry assays, such as glucose, total iron, and total iron binding capacity. The curvatures and the background subtracted signals may allow the assays to be even less sensitive to spectral interference (e.g. hemolysis, icterus, and lipemia).

Applying the Background Subtraction Method in Imaging

For at least one non-limiting example, getting meaningful spectral data from simple imaging (e.g. photography with a simple color camera) is challenging because signals from the whole spectra are combined into a small number of channels (e.g. red, green, and blue in RGB images). One way to obtain spectral data is to use optical filters that allow light to pass through only at specified wavelength ranges. However, it is impractical to set up many optical filters when absorbance values at multiple wavelengths are needed, especially in resource-limited settings. An example of such case is when a hemolysis detection step is required at the collection site (where no spectrophotometer is available) and the detection method requires absorbance values at 5 wavelengths to account for icterus and lipemia.

Figure 9B:
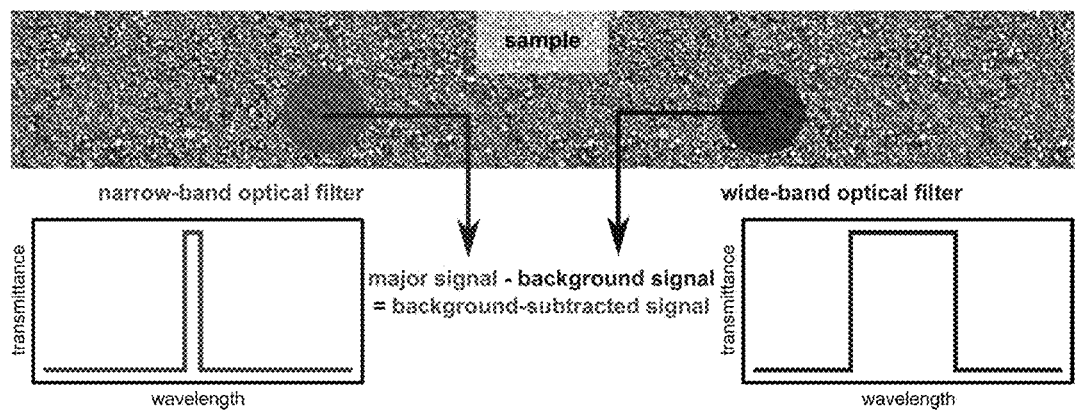
FIG. 9B shows acquisition of background-subtracted signals using a narrow-band optical filter and a wide-band optical filter according to at least one embodiment herein.

Optionally, the background subtraction method can be used in place of methods that require absorbance values at multiple wavelengths to account for spectral interference, such as in the cases of hemolysis and icterus detection/quantification. In one non-limiting example, the novelty is that the background subtraction method only requires 2 optical filters, one with a narrow band to obtain the major signal, and the other one with a wider band to obtain the background signal (FIG. 9B). If the two optical filters are placed in the region of interest at the same time, only one image is used to obtain the background subtracted signal for each sample (FIG. 9B). Such design is compatible with resource-limited settings. For example, to detect hemolysis at the collection site without a spectrophotometer, one can image the plasma fractions of centrifuged collection devices using a simple point-and-shoot camera (or a cell phone camera or other image capture device) with the light path including a hybrid filter with two sides that pass a narrow band and a wide band of wavelengths.

In this non-limiting example, FIG. 9B shows acquisition of background-subtracted signals using a narrow-band optical filter and a wide-band optical filter. If the two filters can be placed in the regions of interest concurrently, only one exposure is needed to obtain the major signal, the background signal, and the background-subtracted signal. The bands are centered near the absorption peak of interest but do not necessary have to be centered at the peak of interest.

Icterus Detection/Quantification with Curvatures

Figure 10:
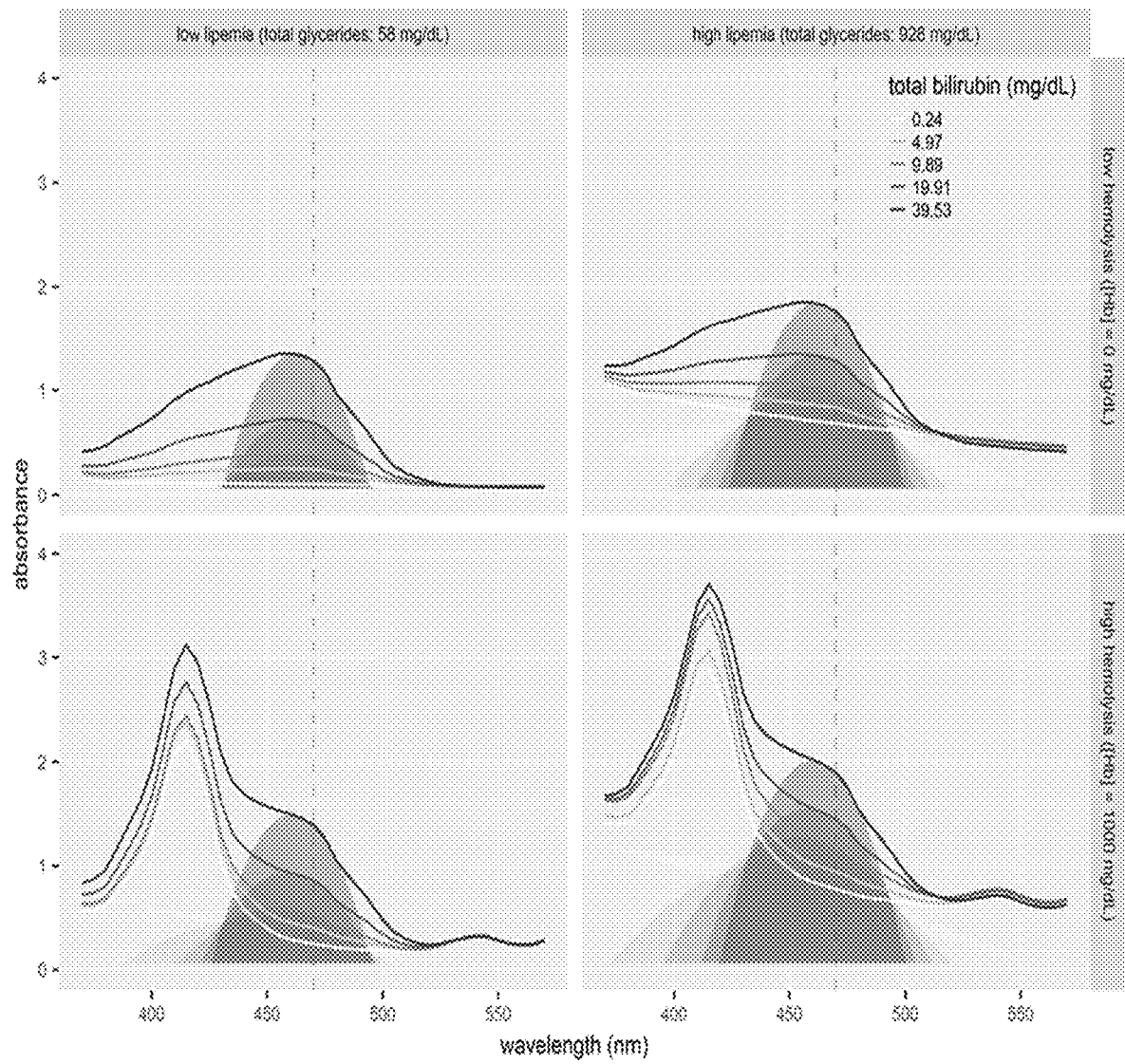
FIG. 10 shows that curvatures can be used to avoid interference from hemolysis and lipemia in icterus detection/quantification according to at least one embodiment herein.

Referring now to FIG. 10, curvatures can be used to avoid interference from hemolysis and lipemia in icterus detection/quantification. The plots show absorption spectra near the bilirubin peak of samples at specified icterus levels (0.24, 4.97, 9.89, 19.91, and 39.53 mg/dL), at combinations of low and high hemolysis and lipemia ([Hb]=0 or 1000 mg/dL; total glycerides=58 or 928 mg/dL). The dashed lines indicate the wavelength of 470 nm (just off the 460-nm peak). The shaded areas indicate circles fitted to the sets of 5 points centered around 470 nm (at 460, 465, 470, 475, and 480 nm). The circles appear to be ellipses because of the different in scales of the absorbance and the wavelength. Each curvature value is the inverse of the corresponding radius.

Figure 11:
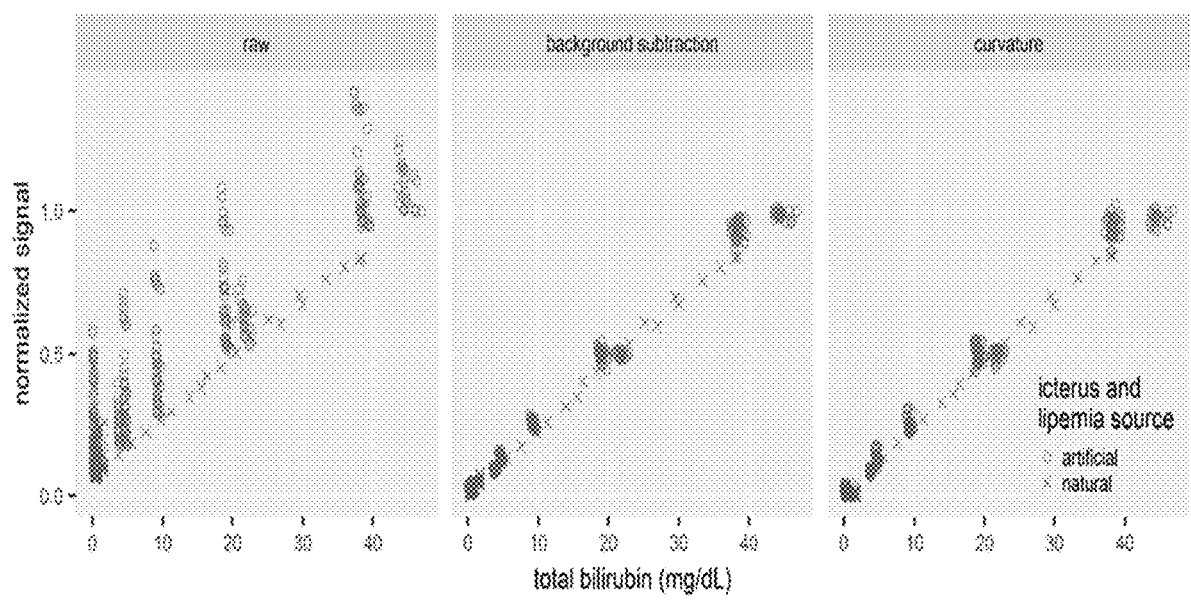
FIG. 11 shows the use of background subtraction and curvature calculation in removing interference signals according to at least one embodiment herein.

For at least one non-limiting example, the curvature of the absorption peak at 460 nm was found to be unsuitable for the quantification/detection of icterus. An optimization step revealed that curvatures at 465 nm and 470 nm (with 3, 5, or 7 points used for the calculation) can be used to quantify icterus levels (via bilirubin concentrations). Very high hemolysis levels (e.g. 1000 mg/dL of [Hb]) can lead to significant interference on the left side of the 460-nm peak (wavelength≤460 nm) but not the right side, so the shape of the absorption curve just off the peak on the right side is not affected by hemolysis (FIG. 10). Results with almost 400 samples show a good correlation between the calculated curvatures and the total bilirubin assay results (FIG. 11). Therefore, the method with curvature calculation can also be used for icterus quantification/detection. Also, in general, the use of this method is not limited to absorption peaks and can be expanded wavelengths near the peaks.

Referring now to FIG. 11, methods can be used based on background subtraction and curvature calculation in removing interference signals for the detection/quantification of icterus (392 samples). The background subtractions were performed using uniform kernels of size 18 (unit=5 nm). The curvatures were calculated using absorbance values at 460, 465, 470, 475, and 480 nm. Artificial sources of icterus and lipemia were conjugated bilirubin and Intralipid®, respectively.

Figure 12:
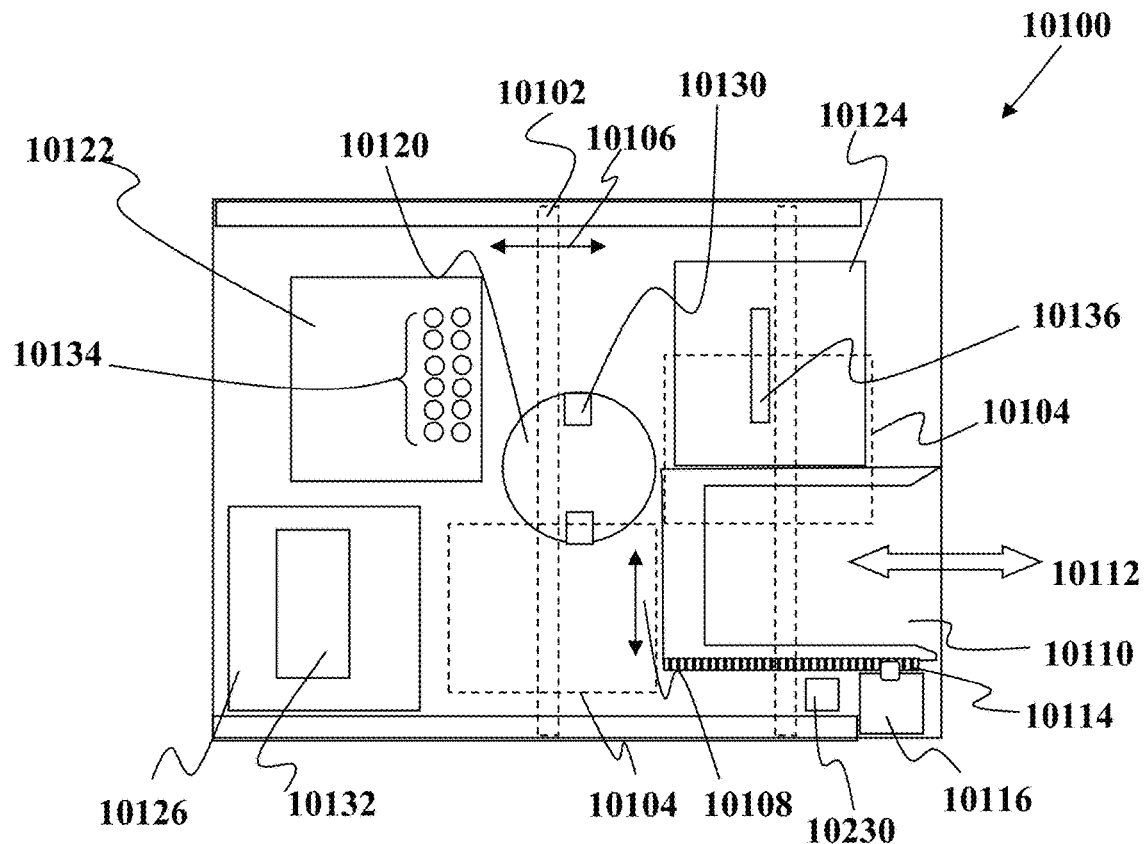
FIGS. 12-16 show embodiments of devices that may be configured to include hardware for implementing one or more embodiments of techniques as described herein.

FIG. 12 shows that there may be an assay station receiving location 10110 configured to receive a cartridge. In one non-limiting example, the assay station receiving location 10110 may be a tray that is movable as indicated by arrow 10112 by the use of motor 10114 and gear tracks 10116 to move the tray outside of the module to facilitate user placement of one or more cartridges into the module.

Once a cartridge is in the system, individual elements of the cartridge such as but not limited to cuvettes, pipette tips, vessels, other physical items, regent(s), fluids, or the like may be moved from the cartridge. FIG. 12 also shows that there may be a variety of components in the module 10100 such as but not limited to a centrifuge 10120, a high sensitivity optical detector 10122 such as but not limited to a PMT, a multi-array optical detector 10124 such as but not limited to a spectrophotometer, and a nucleic acid amplification module 10126. Each of these components may have its own sample vessel receiving location such as but not limited to locations 10130, 10132, 10134, and 10136. In one non-limiting example, the locations 10130, 10132, 10134, and 10136 may be sized to be different shapes, sized to receive different types of vessels, and in the case of the centrifuge, may have a variable location depending on where the centrifuge finishes spinning. A controller of the system is configured to direct sample vessels to the desired locations and be able to accurately place them in the appropriate receiving locations for each of the components.

Figure 13:
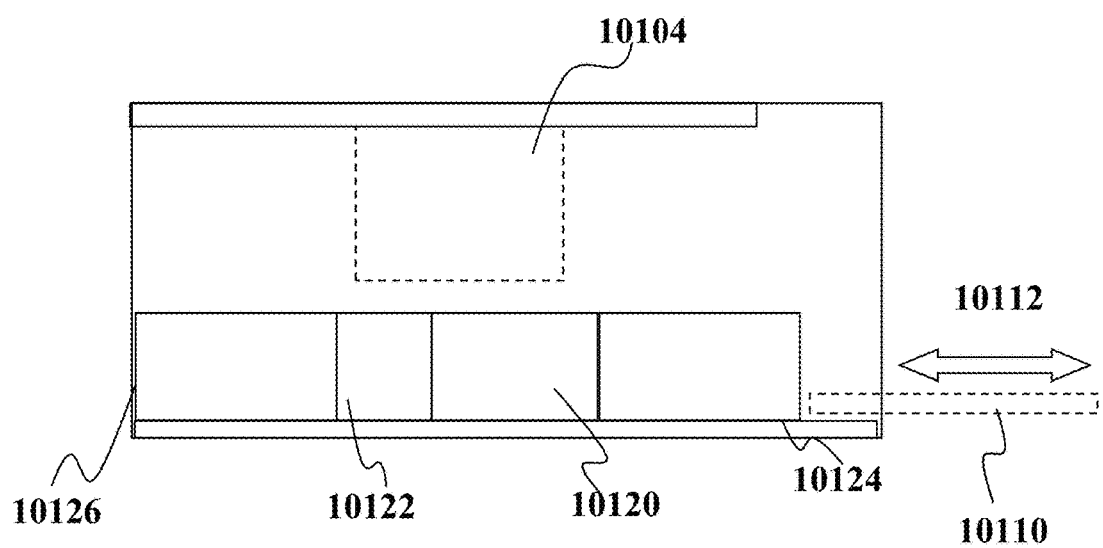

FIG. 13 shows a side view of the various components in the module 10100.

It should also be understood that thermal control of conditions within the module 10100 can be regulated so that thermal conditioning by way of controlled temperature air flow through the system is accomplished so that temperature sensor(s) in the module detect that ambient air in the system is within a desired range. Optionally, the thermal regulation is by way of a combination of controlled air temperature and controlled support structure temperature. This can be of particular use when the support structure comprises of a thermally conductive material.

Figure 14:
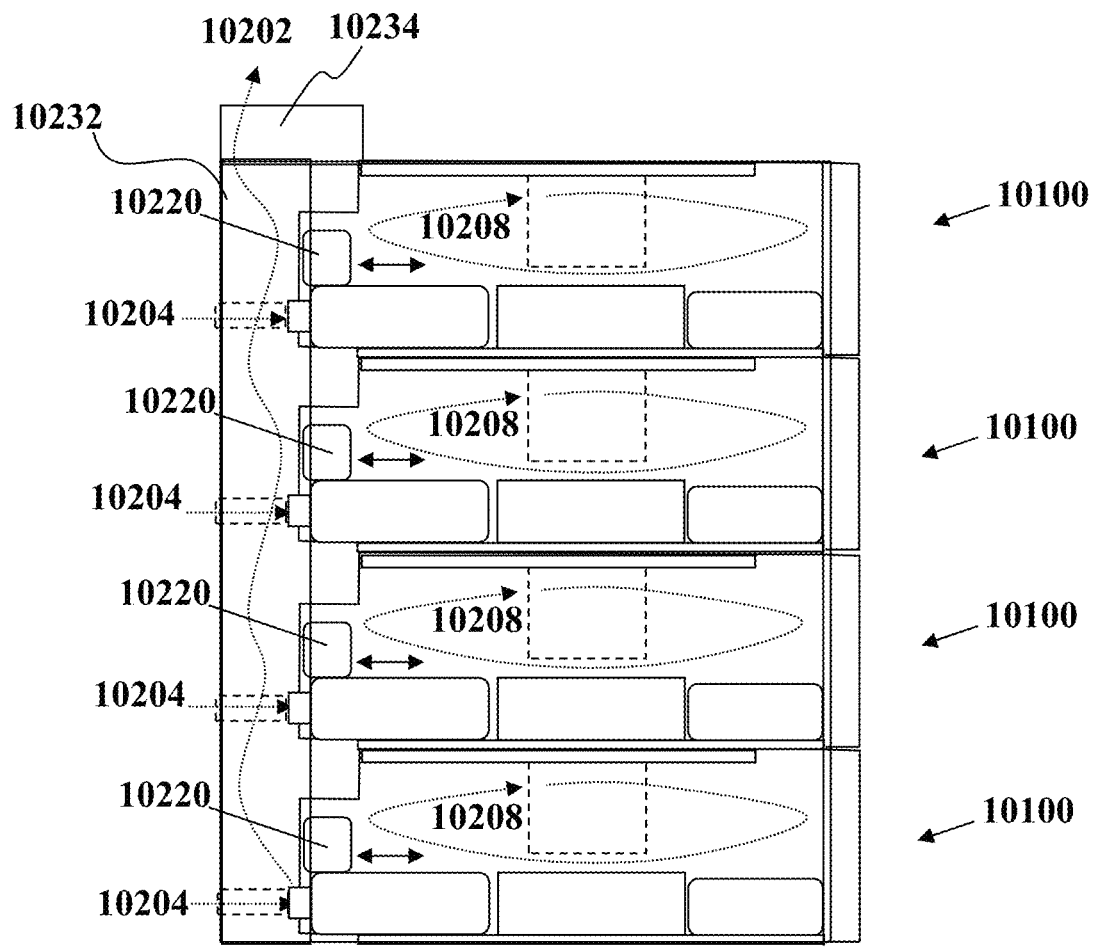

Referring now to FIG. 14, one embodiment of a system 10200 with linked convective flow between modules will now be described. As seen in FIG. 14, the common flow between modules 10100 is shown by arrow 10202. Inlet air flow into each of the modules 10100 is indicated by arrow 10204. Optionally, the thermal conditioning of adjacent modules can be used to condition the underside or other surfaces of adjacent modules. In this manner, combined module thermal conditioning can create a more stable thermal state for all of the modules sharing a common mounting. This convective air flow within a module is indicated by arrow 10208. Optionally, a convective flow unit 10220 which may provide thermally conditioned (heated, cooled, or neutral) airflow can be used to maintain a desired air temperature range within the substantially light tight confines of the modules 10100. One more temperature sensors 10230 may be included in the modules 10100 to provide feedback to a controller to adjust flow rate and/or air temperature coming from device 10220. A fully or at least partially enclosed pathway 10232 may be used to direct exhaust air flow to a filtered outlet 10234 that may have an exhaust fan therein. Optionally, flow can be reversed on the exhaust fan such that it can also function as an inlet if the fan is operated in reversed.

Figure 15:
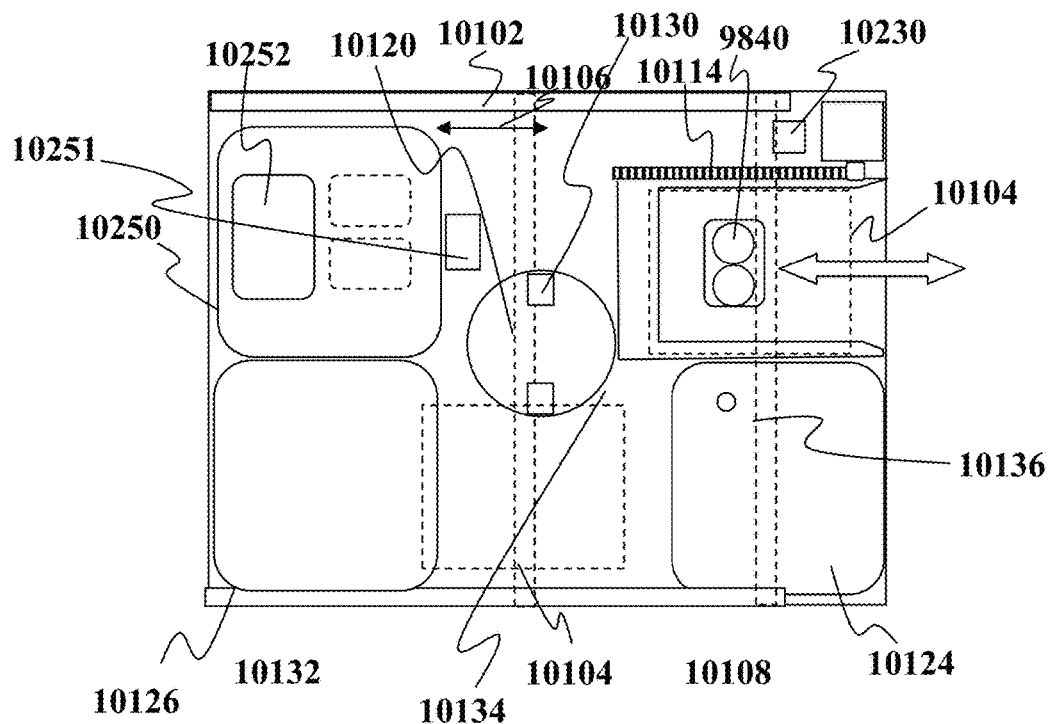
Figure 16:
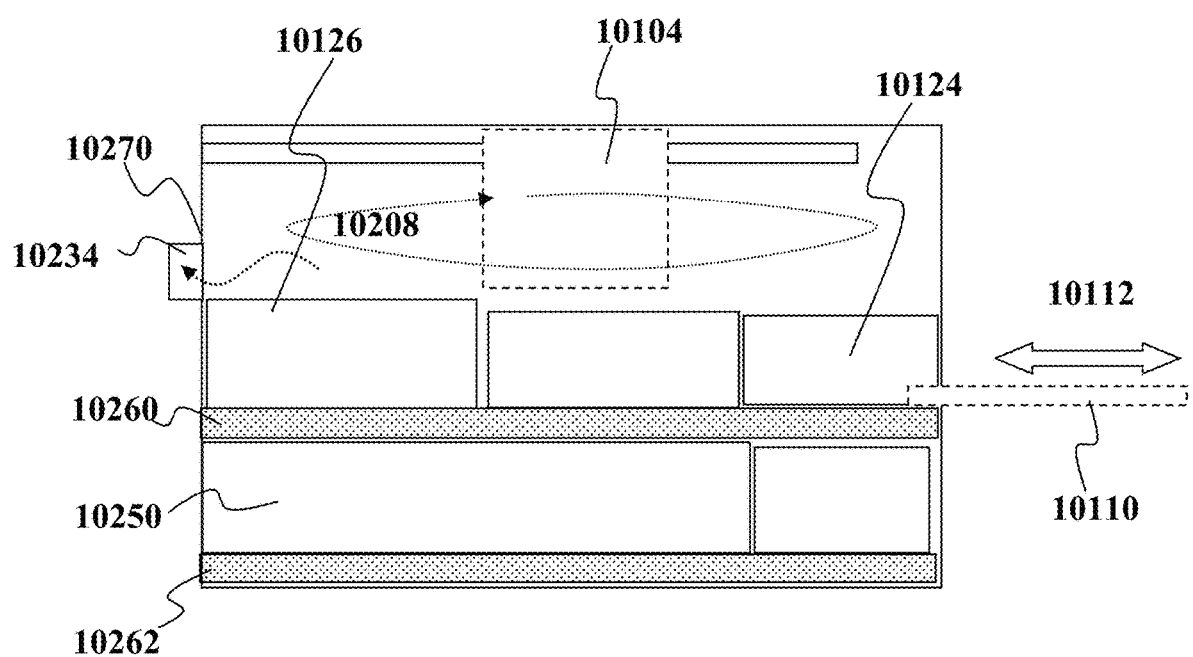

Referring now to FIGS. 15 and 16, optionally, some embodiments may have a bilayer module configuration wherein certain hardware elements are mounted on a first plane while second elements that may have a different height are mounted on a second plane such that the features on the first plane and second plane have sample vessel loading areas in zones or planes accessible by a common pipette system mounted on an XY gantry. By way of non-limiting example, FIG. 15 shows that an optical detector component 10250 may have an upper surface 10252 that is located within the range of motion of the sample handling system with gantry 10102. In one non-limiting example, the upper surface 10252 is above the first support layer 10260 while the device 10250 is mounted on the second support layer 10262. The surface 10252 may be sized to receive one cuvette or multiple cuvettes. FIG. 15 also shows that the pipette 10104 in a second location, or optionally, some systems may use second pipette and gantry system with the module 10100. It should be understood that the housing 10270 may be a light-tight housing. Some embodiments may align a plurality of the bilayer modules in a stack (similar to FIG. 108) and/or horizontal combination wherein all of the resources are contained in each of the bilayer modules. Some may not use any additional transport devices between bilayer modules, but such transport devices are not excluded in alternative embodiments. Optionally, some embodiments may include a module 10251 for detecting and/or correcting for the conditions described herein regarding samples that are lipemic or contain other interferents that are to adjusted, detected, and/or accounted for.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, with any of the above embodiments, it should be understood that the signal processing techniques described herein are not limited to those assays mentioned in the text, but may also be applied to other assays not expressly listed or described herein. It should be understood that the detection and/or correction techniques (or associated hardware) can be integrated into stand-alone device. Optionally, the detection and/or correction techniques (or associated hardware) may be integrated into automated sample analyzers or sample processors. Optionally, they may be part of a sample preparation and/or sample pre-processing stage of the above devices. Optionally, they may be used during various steps/processes of assay processing or analysis.

Additionally, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a size range of about 1 nm to about 200 nm should be interpreted to include not only the explicitly recited limits of about 1 nm and about 200 nm, but also to include individual sizes such as 2 nm, 3 nm, 4 nm, and sub-ranges such as 10 nm to 50 nm, 20 nm to 100 nm, etc. . . . .

The publications discussed or cited herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. All publications mentioned herein are incorporated herein by reference to disclose and describe the structures and/or methods in connection with which the publications are cited. By way of non-limiting example, the following applications are fully incorporated herein by reference for all purposes: 62/452,949 entitled "METHODS AND DEVICES FOR IMPROVED SIGNAL DETECTION FROM BIOLOGICAL SAMPLES" filed Jan. 31, 2017, U.S. Patent Application No. 62/519,018 entitled "Spectral analysis methods based on background subtraction and curvature calculation used in the detection or quantification of hemolysis and icterus in blood-derived clinical samples" filed Jun. 13, 2017, U.S. Pat. Nos. 7,888,125, 8,007,999, 8,088,593 and U.S. Publication No., US20120309636, PCT Application No. PCT US2012/057155, U.S. patent application Ser. No. 13/244,952, and PCT Application No. PCT/US2011/53188, filed Sep. 25, 2011. PCT Application No. PCT/US2011/53188, filed Sep. 25, 2011, U.S. patent application Ser. No. 13/244,946, filed Sep. 26, 2011, PCT Application No. PCT/US11/53189, filed Sep. 25, 2011, Patent Cooperation Treaty Application No. PCT/US2011/53188; Patent Cooperation Treaty Application No. PCT/US2012/57155; U.S. patent application Ser. No. 13/244,947; U.S. patent application Ser. No. 13/244,949; U.S. patent application Ser. No. 13/244,950; U.S. patent application Ser. No. 13/244,951; U.S. patent application Ser. No. 13/244,952; U.S. patent application Ser. No. 13/244,953; U.S. patent application Ser. No. 13/244,954; U.S. patent application Ser. No. 13/244,956; and U.S. application Ser. No. 15/595,489.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. Any feature, whether preferred or not, may be combined with any other feature, whether preferred or not. The appended claims are not to be interpreted as including means-plus-function limitations, unless such a limitation is explicitly recited in a given claim using the phrase "means for." It should be understood that as used in the description herein and throughout the claims that follow, the meaning of "a," "an," and "the" includes plural reference unless the context clearly dictates otherwise. For example, a reference to "an assay" may refer to a single assay or multiple assays. Also, as used in the description herein and throughout the claims that follow, the meaning of "in" includes "in" and "on" unless the context clearly dictates otherwise. Finally, as used in the description herein and throughout the claims that follow, the meaning of "or" includes both the conjunctive and disjunctive unless the context expressly dictates otherwise. Thus, the term "or" includes "and/or" unless the context expressly dictates otherwise.

What is claimed is:

1. A method for use with a biological sample, the method comprising:
   using a camera to image said biological sample in a sample processing device;
   acquiring background-subtracted signals by processing light from said image using a narrow-band optical filter and a wide-band optical filter; and
   using a processor programmed to use said background-subtracted signals for quantification of hemolysis and icterus in the biological sample.

2. A method for use with a biological sample, the method comprising:
   using a camera to image said biological sample in a sample processing device;
   acquiring background-subtracted signals by processing light from said image using a narrow-band optical filter and a wide-band optical filter; and
   using a processor programmed to use said background-subtracted signals for quantification of hemolysis and icterus in the biological sample;
   wherein said using comprises placing the narrow-band optical filter to process light from a first region of interest of said image and placing the wide-band optical filter to process light from a second region of interest concurrently so that only one exposure is needed to obtain the major signal, the background signal, and the background-subtracted signal.

3. A method for use with a biological sample, the method comprising:
- using a camera to image said biological sample in a sample processing device;
- acquiring background-subtracted signals by processing light from said image using a narrow-band optical filter and a wide-band optical filter;
- using a processor programmed to use said background-subtracted signals for quantification of hemolysis and icterus in the biological sample; and
- reducing signal interference through using said programmed processor for the calculation of background-subtracted spectra.

* * * * *